(12) United States Patent
Yang et al.

(10) Patent No.: US 8,367,040 B2
(45) Date of Patent: Feb. 5, 2013

(54) CONTRAST AGENTS AND METHODS FOR PREPARING CONTRAST AGENTS

(75) Inventors: Jenny Jie Yang, Marietta, GA (US); Zhi-Ren Liu, Athens, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 13/451,691

(22) Filed: Apr. 20, 2012

(65) Prior Publication Data

US 2012/0269735 A1 Oct. 25, 2012

Related U.S. Application Data

(62) Division of application No. 11/457,370, filed on Jul. 13, 2006, now Pat. No. 8,173,105.

(60) Provisional application No. 60/699,409, filed on Jul. 13, 2005.

(51) Int. Cl.
*A61K 49/14* (2006.01)
*G01N 33/567* (2006.01)

(52) U.S. Cl. .......... 424/9.34; 424/9.32; 424/9.323; 424/9.341

(58) Field of Classification Search .......... 424/9.32, 424/9.34, 9.341; 435/69.1, 183, 325, 350
See application file for complete search history.

(56) References Cited

U.S. PATENT DOCUMENTS

| | | |
|---|---|---|
| 2002/0123113 A1 | 9/2002 | Tsien et al. |
| 2002/0136692 A1 | 9/2002 | Haroon et al. |
| 2003/0180222 A1 | 9/2003 | Zhang et al. |
| 2004/0115132 A1 | 6/2004 | Young et al. |
| 2004/0171107 A1 | 9/2004 | Nelson et al. |
| 2004/0208827 A1 | 10/2004 | McMurry et al. |
| 2006/0035289 A1 | 2/2006 | Matsudaira et al. |
| 2007/0212305 A1 | 9/2007 | Klaveness et al. |

OTHER PUBLICATIONS

International Search Report and Written Opinion of the International Searching Authority, 2007.
Cohen, B., et al., Ferritin as an Endogenous MRI Reporter for Noninvasive Imaging of Gene Expression in C6 Glioma Tumors, Neoplasia, Feb. 2005, Vo. 7, No. 2, pp. 109-111.
Pessl, A., et al., A designed metal-binding protein with a novel fold [abstract], Nature, Mar. 25, 1993, 362, 367 369 [online].

*Primary Examiner* — Michael G Hartley
*Assistant Examiner* — Jagadishwar Samala
(74) *Attorney, Agent, or Firm* — Thomas Horstemeyer, LLP

(57) ABSTRACT

Contrast agents comprising a scaffold protein having at least one operative integrated metal ion binding site.

6 Claims, 8 Drawing Sheets

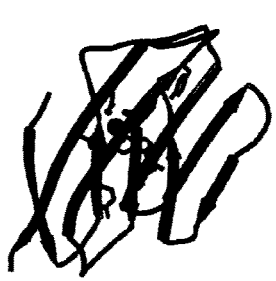 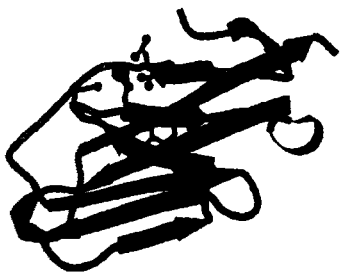 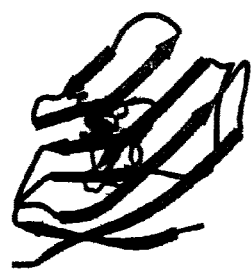
FIG. 1A  FIG. 1B  FIG. 1C
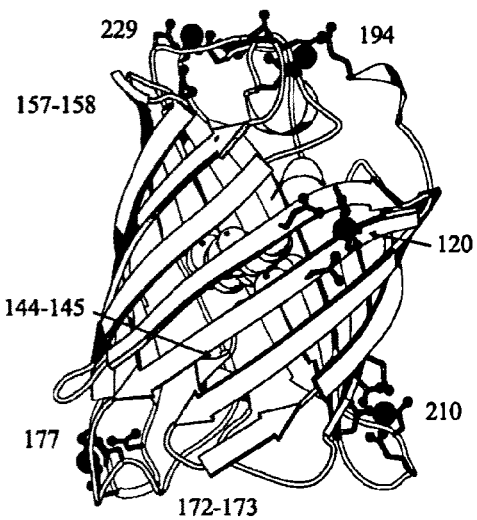 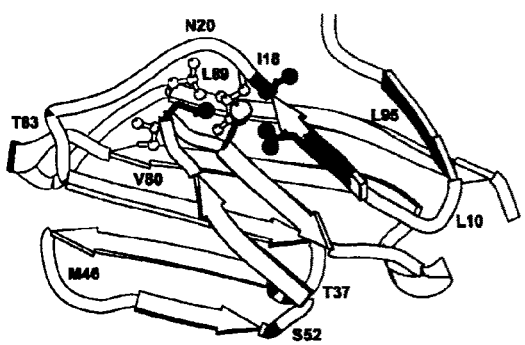
FIG. 1D  FIG. 1E

SEQUENCE LISTING

<160> NUMBER OF SEQ ID NOS: 19

<210> SEQ ID NO 1
<211> LENGTH: 123
<212> TYPE: PRT
<213> ORGANISM: Artificial Sequence
<220> FEATURE:
<223> OTHER INFORMATION: Modified Albumin Sequence

<400> SEQUENCE: 1

```
Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60

Gln Asn Pro His Ser Ser Asn Ile Cys Asn Ile Ser Cys Asp Lys Phe
65                  70                  75                  80

Leu Asp Asp Asp Leu Thr Asp Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
        115                 120
```

<210> SEQ ID NO 2
<211> LENGTH: 99
<212> TYPE: PRT
<213> ORGANISM: Artificial Sequence
<220> FEATURE:
<223> OTHER INFORMATION: Modified CD2 protein

<400> SEQUENCE: 2

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu
```

<210> SEQ ID NO 3
<211> LENGTH: 288
<212> TYPE: PRT
<213> ORGANISM: Artificial Sequence
<220> FEATURE:
<223> OTHER INFORMATION: Modified CD2 with metal binding site (N15E, E56, L58D, D62, and K64D, (EEDDD) )

<400> SEQUENCE: 3

```
Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
    50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
    130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
            180                 185                 190

Glu Glu Ile Arg Glu Ala Phe Arg Val Phe Asp Lys Asp Gly Asn Gly
        195                 200                 205

Tyr Ile Ser Ala Ala Glu Leu Arg His Val Met Thr Asn Leu Asp Gly
    210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 4
<211> LENGTH: 99
<212> TYPE: PRT
<213> ORGANISM: Artificial Sequence
<220> FEATURE:
<223> OTHER INFORMATION: Modified CD2 protein with with metal binding
      site(s): N15E, E56, L58D, D62, and K64N

<400> SEQUENCE: 4

Arg Asp Ser Gly Thr Val Trp Gly Ala Leu Gly His Gly Ile Glu Leu
1               5                   10                  15

Asn Ile Pro Asn Phe Gln Met Thr Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asn
    50                  55                  60

Ile Lys Asn Leu Thr Arg Asp Asp Ser Gly Thr Tyr Asn Val Thr Val
65                  70                  75                  80
```

```
Tyr Ser Thr Asn Gly Thr Arg Ile Leu Asn Lys Ala Leu Asp Ile Arg
                85                  90                  95

Ile Leu Glu

<210> SEQ ID NO 5
<211> LENGTH: 99
<212> TYPE: PRT
<213> ORGANISM: Artificial Sequence
<220> FEATURE:
<223> OTHER INFORMATION: Modified CD2 Protein with metal binding
      site(s): N15E, E56, L58D, D62, and K64Q

<400> SEQUENCE: 5

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Asp Ala Asn Gly Asp Leu Gln
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu

<210> SEQ ID NO 6
<211> LENGTH: 99
<212> TYPE: PRT
<213> ORGANISM: Artificial Sequence
<220> FEATURE:
<223> OTHER INFORMATION: Modified CD2 Protein with metal binding
      site(s): N15, E56, L58N, D62, and K64N

<400> SEQUENCE: 6

Arg Asp Ser Gly Thr Val Trp Gly Ala Leu Gly His Gly Ile Asn Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Asn Ala Asn Gly Asp Leu Asn
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu

<210> SEQ ID NO 7
<211> LENGTH: 288
<212> TYPE: PRT
<213> ORGANISM: Artificial Sequence
<220> FEATURE:
<223> OTHER INFORMATION: Modified CD2 Protein with metal binding sites:
      N15E, E56, L58N, D62, and K64N

<400> SEQUENCE: 7

Met Ala Ser Met Thr Gly Gly Gln Gln Met Gly Arg Gly Ser Gly Pro
```

-continued

```
                1               5                   10                  15
Ser Arg Met Val Ser Lys Gly Glu Glu Leu Phe Thr Gly Val Val Pro
                    20                  25                  30

Ile Leu Val Glu Leu Asp Gly Asp Leu Asn Gly His Lys Phe Ser Val
                    35                  40                  45

Ser Gly Glu Gly Glu Gly Asp Ala Thr Tyr Gly Lys Leu Thr Leu Lys
 50                             55                  60

Phe Ile Cys Thr Thr Gly Lys Leu Pro Val Pro Trp Pro Thr Leu Val
 65                     70                  75                  80

Thr Thr Leu Thr Tyr Gly Val Gln Cys Phe Ser Arg Tyr Pro Asp His
                    85                  90                  95

Met Lys Gln His Asp Phe Phe Lys Ser Ala Met Pro Glu Gly Tyr Val
                    100                 105                 110

Gln Glu Arg Thr Ile Phe Phe Lys Asp Asp Gly Asn Tyr Lys Thr Arg
                    115                 120                 125

Ala Glu Val Lys Phe Glu Gly Asp Thr Leu Val Asn Arg Ile Glu Leu
                    130                 135                 140

Lys Gly Ile Asp Phe Lys Glu Asp Gly Asn Ile Leu Gly His Lys Leu
145                     150                 155                 160

Glu Tyr Asn Tyr Asn Ser His Asn Val Tyr Ile Met Ala Asp Lys Gln
                    165                 170                 175

Lys Asn Gly Ile Lys Val Asn Phe Lys Ile Arg His Asn Ile Glu Glu
                    180                 185                 190

Glu Glu Ile Arg Glu Ala Phe Arg Val Phe Asp Lys Asp Gly Asn Gly
                    195                 200                 205

Tyr Ile Ser Ala Ala Glu Leu Arg His Val Met Thr Asn Leu Asp Gly
                    210                 215                 220

Ser Val Gln Leu Ala Asp His Tyr Gln Gln Asn Thr Pro Ile Gly Asp
225                     230                 235                 240

Gly Pro Val Leu Leu Pro Asp Asn His Tyr Leu Ser Thr Gln Ser Ala
                    245                 250                 255

Leu Ser Lys Asp Pro Asn Glu Lys Arg Asp His Ile Val Leu Leu Glu
                    260                 265                 270

Phe Val Thr Ala Ala Gly Ile Thr Leu Gly Met Asp Glu Leu Tyr Lys
                    275                 280                 285
```

<210> SEQ ID NO 8
<211> LENGTH: 99
<212> TYPE: PRT
<213> ORGANISM: Artificial Sequence
<220> FEATURE:
<223> OTHER INFORMATION: Modified CD2 protein with metal binding
      site(s): E29, R31D, E41, and K43D

<400> SEQUENCE: 8

```
Arg Asp Ser Gly Thr Val Trp Gly Ala Leu Gly His Gly Ile Asn Leu
 1               5                   10                  15

Asn Ile Pro Asn Phe Gln Met Thr Asp Asp Ile Asp Glu Val Asp Trp
                    20                  25                  30

Glu Arg Gly Ser Thr Leu Val Ala Glu Phe Asp Arg Lys Met Lys Pro
                    35                  40                  45

Phe Leu Lys Ser Gly Ala Phe Glu Ile Asn Ala Asn Gly Asp Leu Lys
                    50                  55                  60

Ile Lys Asn Leu Thr Arg Asp Asp Ser Gly Thr Tyr Asn Val Thr Val
 65                     70                  75                  80

Tyr Ser Thr Asn Gly Thr Arg Ile Leu Asn Lys Ala Leu Asp Ile Arg
```

Ile Leu Glu

<210> SEQ ID NO 9
<211> LENGTH: 99
<212> TYPE: PRT
<213> ORGANISM: Artificial Sequence
<220> FEATURE:
<223> OTHER INFORMATION: Modified CD2 with metal binding site(s): E29, R31K, E41, and K43D

<400> SEQUENCE: 9

```
Arg Asp Ser Gly Thr Val Trp Gly Ala Leu Gly His Gly Ile Asn Leu
1               5                   10                  15

Asn Ile Pro Asn Phe Gln Met Thr Asp Asp Ile Asp Glu Val Lys Trp
            20                  25                  30

Glu Arg Gly Ser Thr Leu Val Ala Glu Phe Asp Arg Lys Met Lys Pro
        35                  40                  45

Phe Leu Lys Ser Gly Ala Phe Glu Ile Asn Ala Asn Gly Asp Leu Lys
50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu
```

<210> SEQ ID NO 10
<211> LENGTH: 288
<212> TYPE: PRT
<213> ORGANISM: Artificial Sequence
<220> FEATURE:
<223> OTHER INFORMATION: Modifed GFP with metal binding site(s): N77, T79D, N90, and A92E

<400> SEQUENCE: 10

```
Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
    130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
```

```
                180                 185                 190
Glu Glu Ile Arg Glu Ala Phe Arg Val Phe Asp Lys Asp Gly Asn Gly
            195                 200                 205

Tyr Ile Ser Ala Ala Glu Leu Arg His Val Met Thr Asn Leu Asp Gly
        210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 11
<211> LENGTH: 288
<212> TYPE: PRT
<213> ORGANISM: Artificial Sequence
<220> FEATURE:
<223> OTHER INFORMATION: Modified CD2 with metal binding loop III of
      calmodulin flanked by 5 glycine residues (3 and 2 at both ends)
      grafted at position 52

<400> SEQUENCE: 11

Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
            85                  90                  95

Met Lys Gln His Asp Phe Phe Lys Ser Ala Met Pro Glu Gly Tyr Val
        100                 105                 110

Gln Glu Arg Thr Ile Phe Phe Lys Asp Asp Gly Asn Tyr Lys Thr Arg
            115                 120                 125

Ala Glu Val Lys Phe Glu Gly Asp Thr Leu Val Asn Arg Ile Glu Leu
        130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
            180                 185                 190

Glu Glu Ile Arg Glu Ala Phe Arg Val Phe Asp Lys Asp Gly Asn Gly
        195                 200                 205

Tyr Ile Ser Ala Ala Glu Leu Arg His Val Met Thr Asn Leu Asp Gly
        210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255
```

```
Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 12
<211> LENGTH: 99
<212> TYPE: PRT
<213> ORGANISM: Artificial Sequence
<220> FEATURE:
<223> OTHER INFORMATION: Modified CD2 with metal binding site(s): E29,
      R31K, E41, and K43D

<400> SEQUENCE: 12

Arg Asp Ser Gly Thr Val Trp Gly Ala Leu Gly His Gly Ile Asn Leu
1               5                   10                  15

Asn Ile Pro Asn Phe Gln Met Thr Asp Asp Ile Asp Glu Val Lys Trp
            20                  25                  30

Glu Arg Gly Ser Thr Leu Val Ala Glu Phe Asn Arg Lys Met Lys Pro
        35                  40                  45

Phe Leu Lys Ser Gly Ala Phe Glu Ile Asn Ala Asn Gly Asp Leu Lys
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu

<210> SEQ ID NO 13
<211> LENGTH: 99
<212> TYPE: PRT
<213> ORGANISM: Artificial Sequence
<220> FEATURE:
<223> OTHER INFORMATION: Modified CD2 with metal binding site(s): N15D,
      N17D, N60, and D62

<400> SEQUENCE: 13

Arg Asp Ser Gly Thr Val Trp Gly Ala Leu Gly His Gly Ile Asp Leu
1               5                   10                  15

Asp Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Leu Ala Asn Gly Asp Leu Lys
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Ile Arg
                85                  90                  95

Ile Leu Glu

<210> SEQ ID NO 14
<211> LENGTH: 116
<212> TYPE: PRT
<213> ORGANISM: Artificial Sequence
<220> FEATURE:
<223> OTHER INFORMATION: Modified CD2 with with metal binding loop III
      of calmodulin flanked by 5 glycine residues (3 and 2 at both ends)
      grafted at position 52

<400> SEQUENCE: 14
```

-continued

```
Arg Asp Ser Gly Thr Val Trp Gly Ala Leu Gly His Gly Ile Asn Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Asp Lys Asp Gly Asn Gly Tyr Ile Ser
    50                  55                  60

Ala Ala Glu Gly Gly Gly Ala Phe Glu Ile Leu Ala Asn Gly Asp Leu
65              70                  75                  80

Lys Ile Lys Asn Leu Thr Arg Asp Asp Ser Gly Thr Tyr Asn Val Thr
                85                  90                  95

Val Tyr Ser Thr Asn Gly Thr Arg Ile Leu Asn Lys Ala Leu Asp Ile
            100                 105                 110

Arg Ile Leu Glu
        115
```

<210> SEQ ID NO 15
<211> LENGTH: 128
<212> TYPE: PRT
<213> ORGANISM: Artificial Sequence
<220> FEATURE:
<223> OTHER INFORMATION: Modified CD2 with metal binding site EF-hand
      III from calmodulin grafted at position 52

<400> SEQUENCE: 15

```
Arg Asp Ser Gly Thr Val Trp Gly Ala Leu Gly His Gly Ile Asn Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Glu Glu Glu Ile Arg Glu Ala Phe Arg Val Phe Asp Lys
    50                  55                  60

Asp Gly Asn Gly Tyr Ile Ser Ala Ala Glu Leu Arg His Val Met Thr
65              70                  75                  80

Asn Leu Ala Phe Glu Ile Leu Ala Asn Gly Asp Leu Lys Ile Lys Asn
                85                  90                  95

Leu Thr Arg Asp Asp Ser Gly Thr Tyr Asn Val Thr Val Tyr Ser Thr
            100                 105                 110

Asn Gly Thr Arg Ile Leu Asn Lys Ala Leu Asp Ile Arg Ile Leu Glu
        115                 120                 125
```

<210> SEQ ID NO 16
<211> LENGTH: 288
<212> TYPE: PRT
<213> ORGANISM: Artificial Sequence
<220> FEATURE:
<223> OTHER INFORMATION: Modified Fluorescent protein

<400> SEQUENCE: 16

```
Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
    50                  55                  60
```

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
    130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Glu Glu Glu Ile Arg Glu Ala Phe Arg Val Phe Asp Lys Asp Gly Asn
            180                 185                 190

Gly Tyr Ile Ser Ala Ala Glu Leu Arg His Val Met Thr Asn Leu Lys
        195                 200                 205

Asn Gly Ile Lys Val Asn Phe Lys Ile Arg His Asn Ile Glu Asp Gly
    210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 17
<211> LENGTH: 288
<212> TYPE: PRT
<213> ORGANISM: Artificial Sequence
<220> FEATURE:
<223> OTHER INFORMATION: Modified GFP with metal binding site EF-hand
      III from calmodulin grafted at position 157

<400> SEQUENCE: 17

Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
    50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
    130                 135                 140

```
Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Glu Glu Glu Ile Arg Glu Ala Phe Arg Val Phe Asp Lys Asp Gly Asn
            180                 185                 190

Gly Tyr Ile Ser Ala Ala Glu Leu Arg His Val Met Thr Asn Leu Lys
        195                 200                 205

Asn Gly Ile Lys Val Asn Phe Lys Ile Arg His Asn Ile Glu Asp Gly
    210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

<210> SEQ ID NO 18
<211> LENGTH: 288
<212> TYPE: PRT
<213> ORGANISM: Artificial Sequence
<220> FEATURE:
<223> OTHER INFORMATION: Modifed GFP - the Metal binding site is the EF
      hand III from Calmodulin and is grafted at positon 172

<400> SEQUENCE: 18

Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
    50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
    130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
            180                 185                 190

Glu Glu Ile Arg Glu Ala Phe Arg Val Phe Asp Lys Asp Gly Asn Gly
        195                 200                 205

Tyr Ile Ser Ala Ala Glu Leu Arg His Val Met Thr Asn Leu Asp Gly
    210                 215                 220
```

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
            245                 250                 255

Leu Ser Lys Asp Pro Asn Glu Lys Arg Asp His Ile Val Leu Leu Glu
        260                 265                 270

Phe Val Thr Ala Ala Gly Ile Thr Leu Gly Met Asp Glu Leu Tyr Lys
        275                 280                 285

<210> SEQ ID NO 19
<211> LENGTH: 308
<212> TYPE: PRT
<213> ORGANISM: Artificial Sequence
<220> FEATURE:
<223> OTHER INFORMATION: Modified GFP

<400> SEQUENCE: 19

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Gly Pro Ser Arg Met Val Ser Lys Gly Glu Glu Leu Phe Thr
        35                  40                  45

Gly Val Val Pro Ile Leu Val Glu Leu Asp Gly Asp Leu Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Glu Glu Glu Ile Arg Glu Ala Phe Arg Val Phe Asp
        195                 200                 205

Lys Asp Gly Asn Gly Tyr Ile Ser Ala Ala Glu Leu Arg His Val Met
    210                 215                 220

Thr Asn Leu Lys Asn Gly Ile Lys Val Asn Phe Lys Ile Arg His Asn
225                 230                 235                 240

Ile Glu Asp Gly Ser Val Gln Leu Ala Asp His Tyr Gln Gln Asn Thr
                245                 250                 255

Pro Ile Gly Asp Gly Pro Val Leu Leu Pro Asp Asn His Tyr Leu Ser
            260                 265                 270

Thr Gln Ser Ala Leu Ser Lys Asp Pro Asn Glu Lys Arg Asp His Ile
        275                 280                 285

Val Leu Leu Glu Phe Val Thr Ala Ala Gly Ile Thr Leu Gly Met Asp
    290                 295                 300

```
Glu Leu Tyr Lys
305
```

CONTRAST AGENTS AND METHODS FOR PREPARING CONTRAST AGENTS

STATEMENT OF RELATED APPLICATIONS

This application is a Divisional of application Ser. No.: 11/457,370 filed on Jul. 13, 2006 entitled Contrast Agents and Methods for Preparing Contrast Agents and claims priority to U.S. Provisional Patent Application No. 60/699,409 entitled "Contrast Agents and Methods for Preparing Contrast Agents" having a filing date of 13 Jul. 2005, which is incorporated herein by reference in its entirety.

BACKGROUND OF THE INVENTION

1. Technical Field

This invention relates to diagnostic imaging, and more particularly to novel contrast agent preparations and their use in diagnostic imaging, for example in visualizing tissue.

2. Prior Art

Imaging technology, including magnetic resonance imaging (MRI), X-ray, positron emission tomography (PET), magnetography, and computed tomography (CT) scanning, has a vital role in the detection and treatment of cancer lesions and other illnesses. For example, MRI technology provides a powerful, non-invasive tool to map and explore the structure and function of soft tissues. In fact, MRI through the use of high-strength magnets and radio-frequency signals can produce three-dimensional images of tissues. Using mechanical imaging system, it is possible to detect neoplastic lesions; the detection of early tumor lesions and metastases still remains challenging.

Contrast agents have been used to improve the intrinsic contrast of the images from imaging technology. This method relies on the administration of contrast agents to amplify the contrast in imaging between the pathological tissue and the normal tissue. The most widely used class of MRI contrast agents are based on gadolinium ion ($Gd^{3+}$), manganese ion ($Mn^{2+}$), and iron ion ($Fe^{3+}$) chelates that are strictly extracellular low molecular weight compounds with T1 relaxivity such as diethylenetriaminepentaacetate (DTPA). Ultimately, the efficacy of a contrast agent depends on both the inherent capability to improve images and the pharmacokinetics.

For example, the $Gd^{3+}$ based contrast agents approved for clinical use are mainly non-specific small molecules. Such $Gd^{3+}$ contrast agents usually have relaxivities of <10 $mM^{-1}s^{-1}$ which are 20 to 50 fold lower than the predicted values. The relaxivities are mainly limited by the rotational correlation time of the molecule. The most commonly used contrast agent, DTPA, has a R1 relaxivity of 5 $mM^{-1}s^{-1}$. With this relaxivity, a robust clinical examination usually requires a large dose (>0.1 mM local concentration) in order to reach sufficient contrast or to produce an acceptable image. In addition, this class of contrast agents has a very short circulation time that limits the time window for data collection. Efforts to improve such contrast agents have included the covalent or the non-covalent linkage of the small Gd agent to the macromolecules, such as dendrimers or copolymers.

Accordingly, there is always a need for improved contrast agents with higher capabilities to enhance imaging signals. There also is a need for novel protein-based MRI contrast agents with wide applicability in molecular imaging of various tissues, tumors, cancers, and diseases. There also is a need for contrast agents that can be retained longer in tissue and blood vessels, especially in that of animals and humans. There also is a need for contrast agents in which the chelating site may be tailored for specific applications and the imaging techniques. It is to these needs among others that this invention is directed.

BRIEF SUMMARY OF THE INVENTION

Briefly, this invention is directed to a novel group of contrast agents having tuned properties for diagnostic imaging. More particularly, this invention is directed to a class of magnetic resonance imaging contrast agents that accumulates in tissue. The novel contrast agents comprise a scaffold protein that can be an organic polymer such as a protein and at least one tailored metal ion binding site capable of chelating paramagnetic and heavy metal ions. The at least one tailored metal ion binding site is integrated into select folding pockets within the scaffold protein. In most cases, more than one site can be integrated into the scaffold protein.

The novel contrast agents can be developed by designing tailored binding sites and integrating these sites into scaffold proteins. The binding site can be developed by a design approach or by a grafting approach. Further, other approaches, known or developed hereafter, can be used to design binding sites suitable with this invention. After the site has been developed, the site or sites are operatively integrated into the select areas of the scaffold protein. The contrast agent then may be administered to animals or humans through known delivery methods.

These features, and other features and advantages of the present invention, will become more apparent to those of ordinary skill in the relevant art when the following detailed description of the preferred embodiments is read in conjunction with the appended drawings in which like reference numerals represent like components throughout the several views.

BRIEF DESCRIPTION OF THE DRAWINGS

FIG. 1A shows an exemplary contrast agent prepared according to this invention.

FIG. 1B shows another exemplary contrast agent prepared according to this invention.

FIG. 1C shows another exemplary contrast agent prepared according to this invention.

FIG. 1D shows another exemplary contrast agent prepared according to this invention.

FIG. 1E shows another exemplary contrast agent prepared according to this invention.

DEFINITIONS

Figure 2:
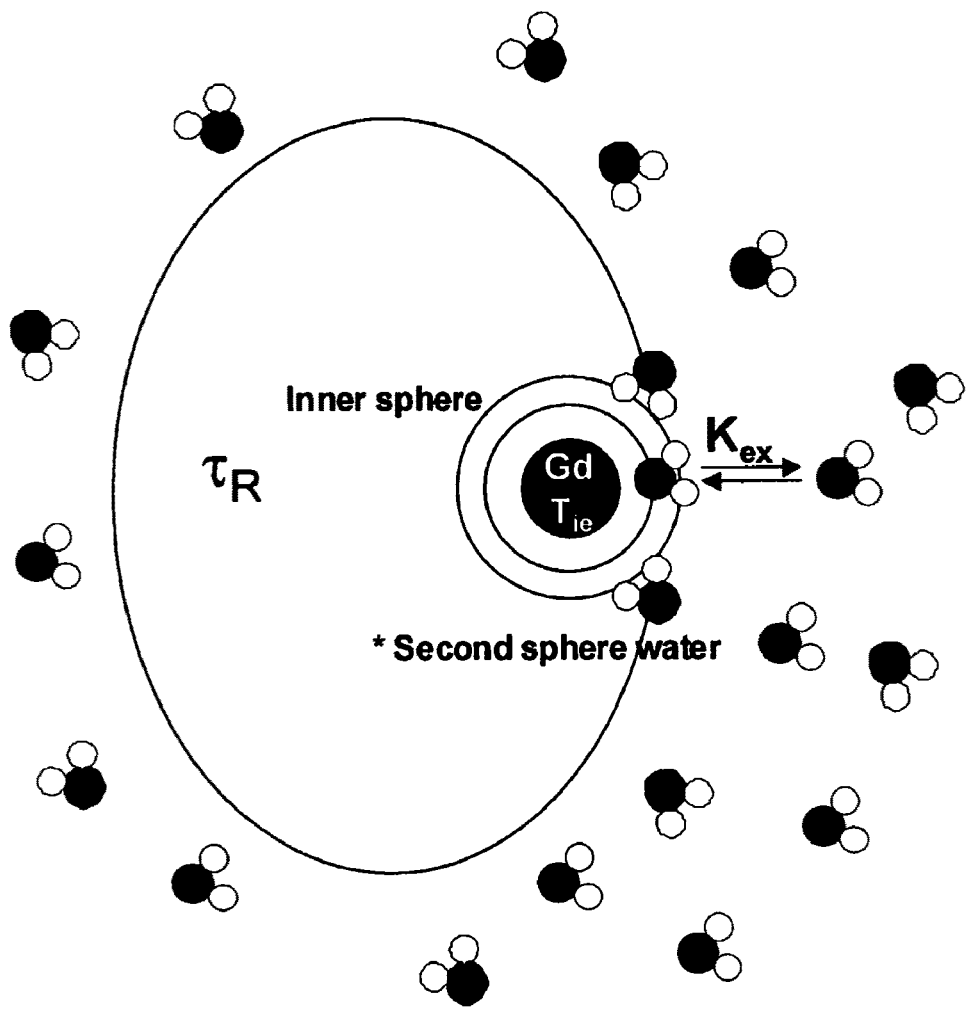
FIG. 2 is a schematic diagram of a contrast agent according to an illustrative embodiment of this invention.

Unless specifically indicated otherwise, all technical and scientific terms used herein have the same meaning as commonly understood by those of ordinary skill in the art to which this invention belongs. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. For example, This term can refer to single and double stranded forms of DNA or RNA.

The term "recombinant nucleic acid molecule" refers to a non-naturally occurring polynucleotide containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein linked to a polypeptide of interest. The term "recombinant host cell" refers to a cell that contains or can express a recombinant nucleic acid molecule.

The term "encoding" in the context of a polypeptide refers to the transcription of the polynucleotide and translation of the mRNA produced therefrom. The encoding polynucleotide is considered to include both the coding strand, whose nucleotide sequence can be identical to an mRNA, as well as its complementary strand. It will be recognized that encoding polynucleotides are considered to include degenerate nucleotide sequences, which encode the same amino acid residues. Nucleotide sequences encoding a polypeptide can include polynucleotides containing introns and exons. Nucleic acid sequences are readily apparent from amino acid sequence and vice versa.

The term "control sequences" refer to polynucleotide sequences that are necessary to effect the expression of coding and non-coding sequences. Such control sequences can include a promoter, a ribosomal binding site, and a transcription termination sequence. The term "control sequences" is intended to include, at a minimum, components whose presence can influence expression and can also include additional components whose presence is advantageous. For example, leader sequences and fusion partner sequences are control sequences.

The term "operatively incorporated" or the like refers to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein can be fused to a polypeptide of interest and in the fused state retain its fluorescence while the polypeptide of interest retains its original biological activity.

As used herein, the term "brightness," with reference to a fluorescent protein, is measured as the product of the extinction coefficient (EC) at a given wavelength and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "polypeptide" or "protein" refers to a polymer of two or more amino acid residues. "Polypeptides" or "proteins" are polymers of amino acid residues that are connected through amide bonds. As defined herein, peptides are inclusive of both natural amino acids and unnatural amino acids (e.g. beta-alanine, phenylglycine, and homoarginine). While amino acids are alpha-amino acids, which can be either of the L-optical isomer or the D-optical isomer, the L-optical isomers are preferred. Such amino acids can be commonly encountered amino acids that are not gene-encoded, although preferred amino acids are those that are encodable.

The term "isolated" or "purified" refers to a material that is substantially or essentially free from components that normally accompany the material in its native state in nature. Purity generally can be determined using analytical chemistry techniques such as polyacrylamide gel electrophoresis, high performance liquid chromatography, and the like. A polynucleotide or a polypeptide is considered to be isolated when it is the least predominant species present in a preparation.

The term "naturally-occurring" refers to a protein, nucleic acid molecule, cell, or other material that occurs in nature. A naturally occurring material can be in its form as it exists in nature, and can be modified by the hand of man such that, for example, it is in an isolated form.

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

Two or more amino acid sequences or two or more nucleotide sequences are considered to be "similar" if the amino acid sequences or the nucleotide sequences share at least 50% sequence identity with each other, or with a reference sequence over a given comparison window. Thus, substantially similar sequences include nucleotide sequences considered to be "substantially identical" or "substantially similar".

The term "fluorescent properties" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

The term "fluorescent protein" refers to any protein capable of light emission when excited with an appropriate electromagnetic energy. Fluorescent proteins include proteins having amino acid sequences that are either natural or engineered, such as the fluorescent proteins derived from *Aequorea victoria* fluorescent proteins.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

DETAILED DESCRIPTION OF THE PREFERRED EMBODIMENTS

Embodiments of this invention include contrast agents capable of enhancing image contrast by affecting water molecule proton relaxation rates. Such contrast agents are effective for magnetic resonance imaging, in part, because the water proton relaxation rate in the target tissue is affected differently than the relaxation rate of the water protons in the surrounding tissue. The contrast agents as disclosed herein are paramagnetic species, which form complexes with metal ions, so to alter the relaxation rates of adjacent nuclei.

More particularly, this invention is directed to a novel group of diagnostic contrast agents having tuned properties, even more particularly, to a class of magnetic resonance contrast agents that accumulates in tissue. The novel contrast agent comprises (a) a scaffold protein that can be an organic polymer such as a protein and (b) at least one tailored metal ion binding site capable of chelating paramagnetic and heavy metal ions, wherein the at least one tailored metal ion binding site is integrated into select folding pockets within the scaffold protein.

The novel contrast agents can be developed by designing tailored binding sites and operatively integrating these sites into scaffold proteins. As will be discussed later in more detail, the binding site may be developed by a design approach or by a grafting approach. After the site has been developed, the site or sites are operatively integrated into the select areas of the scaffold protein. The contrast agent then may be administered to animals or humans through known delivery methods.

In illustrative embodiments, at least one of the metal chelating sites is embedded in the scaffold protein. In such an embodiment, the metal chelating site can be placed within the scaffold protein such that the metal chelating sites are within the interior of the contrast agent. Preferably, at least one of the metal chelating sites is embedded using amino acids of the scaffold proteins as ligands to chelate the metal ion. More preferably, the at least one metal binding site is embedded within the protein such that the scaffold protein has a correlation at least in part resembling the protein itself.

In illustrative embodiments, the scaffold protein for MRI applications is a protein that will host the tailored metal ion binding sites and has the following characteristics:

(a) stability in a physiological environment against cleavage and denaturation;

(b) a topology suitable for the integration of metal ion sites;

(c) a rotational correlation time optimized for the magnetic field (e.g. around 100 milliseconds in a magnetic flied of 1.3 to 3T), e.g. higher magnetic field application can be prepared by changing the site of the protein; and (d) a water exchange rate such that the relaxivity of the protein is not limited by the water exchange rate.

Preferred properties of the scaffold protein also may include water solubility, low interaction with the other cellular metal ions and low toxicity. While of all these properties are not required, the optimal properties of the scaffold protein can and do depend on the specific parameters of the imaging application.

One important property of the scaffold protein is its ability to accept the introduction of metal ion binding sites therein. Preferably, the scaffold protein has a folded conformation, three-dimensional structure or an amino sequence with some homology to the proteins whose structure has been solved at least in part. For example, the scaffold protein can be screened to determine whether it can tolerate the integration of various binding sites without excessive denaturation. For example, the integration of metal ion binding sites into the scaffold protein should not denature or unfold the protein. Thus, the metal ion binding site should not be placed by mutating a hydrophobic core or in a position that results in substantial structural perturbation. This can be examined by sequence alignment of proteins in the same family. Preferably, the amino acids that have an essential role in folding of the structure or the function will be conserved among different species of this same type of the protein.

In another embodiment, the scaffold protein can be a natural protein that chelates a metal ion. In such embodiments, it is possible to modify the natural metal binding sites to chelate heavy metals or paramagnetic metals or other metals useful in diagnostic imaging. For example, it is possible to tailor the amino acid sequence of the scaffold protein that ordinarily binds $Ca^{2+}$ to bind $Gd^{3+}$ by modifying nitrogen or oxygen molecules contained therein.

Preferably, metal ion binding sites are placed into a scaffold protein such that the metal is able to be tumbled together with the protein. It is better to find a location that is not as flexible as or is the same flexibility as the protein body so as to match the correction time. In this case, it is preferred to design or create the binding pocket in the protein. Although insertion also should work, it is preferable to do so in a relatively not so flexible region. Usually the protein can be checked by looking at the B factor (temperature factor for X-ray) or $S^2$ factor (dynamic flexibility factor for NMR) of the pdb (protein data bank) file of the structure.

More than one metal binding site may be integrated into a scaffold protein. The inclusion of more than one binding site improves the sensitivity of the contrast agent. Further, in cases where more than one binding site is integrated into the protein, the site could have different affinities but should still have strong enough affinity for the selected metal so to avoid competition with physiological metal ions. Both metal ions should be embedded into the host protein with preferred rotational correlation times and water exchange rates to provide MRI contrast with an increased sensitivity.

In preferred embodiments, the contrast agents can have a high affinity to and can preferentially select a particular metal ion (e.g. $Gd^{3+}$, $Mn^{2+}$ or $Fe^{3+}$). In one example, exemplary contrast agents showed a dissociation constant $K_d$ less than $10^8$ [M] for $Gd^{3+}$ in an environment having physiological metal ions and prevented those metal ions from precipitation under physiological conditions. Thus, the present invention may be used to create contrast agents having optimal selectivity for a specific metal ion.

The present invention can provide a new mechanism to increase the relaxivity of contrast agents. This is accomplished by designing the metal ion binding sites, e.g. $Gd^{3+}$, in proteins, which can eliminate the mobility and flexibility of the chelating moiety associated with currently available contrast agents. More particularly, by tailoring the binding site, it is possible to prepare contrast agents with higher relaxivity. High proton relaxivity by contrast agents can further enhance images.

One advantage of the present invention is that it provides contrast agents that can preferentially chelate a specific metal ion. For example, a preferred contrast agent having $Gd^{3+}$ binding site(s) will preferentially chelate $Gd^{3+}$ over other metal ions, such as $Mg^{2+}$ or $Ca^{2+}$. As heavy metals tend to be toxic to cells and animals, contrast agents that are able to form a stronger bond with the metal ion are less toxic. As such, the ability to preferentially chelate a specific metal ion can improve the specificity of a contrast agent and can reduce the cytotoxicity of the contrast agent.

In another embodiment, a fusion protein or a non-degradable particle moiety can be added to the protein contrast agent with a linker to tune the correlation time for optimal contrast sensitivity, targeting (subcellular, cellular, tissue and organ selectivity), biodistribution, and bioelimination. One of ordinary skill in the art may determine such linkers without undue experimentation.

In another embodiment, this invention can be used to produce microspheres of contrast agents of low density. These microspheres can have an internal void volume that can be at least about 75% of the total volume of the microsphere. The microspheres may be of varying size, provided they are low density. Suitable size microspheres include those ranging from between about 1 and about 1000 microns in outside diameter.

The contrast agents of the present invention may be formulated with conventional pharmaceutical or veterinary mechanisms and materials. The contrast agent compositions of the present invention may be in conventional pharmaceutical administration forms such as powders, solutions, suspensions, dispersions, etc.; however, solutions, suspensions and dispersions in physiologically acceptable carrier media, for example water for injections, will generally be preferred. For example, such materials include emulsifiers, fatty acid esters, gelling agents, stabilizers, antioxidants, osmolality adjusting agents, buffers, preservatives, antimicrobial agents, and pH adjusting agents. The compositions according to the invention can therefore be formulated for administration using physiologically acceptable carriers or excipients in a manner fully within the skill of the art.

The administration of the contrast agents of this invention can be done in a variety of ways, including, but not limited to, orally, subcutaneously, intravenously, intranasally, transdermally, intraperitoneally, intramuscularly, intrapulmonary, vaginally, rectally, or intraocularly. Preferably, the delivery mechanisms include parenteral administration (injection or infusion directly). Depending upon the manner of introduction, the compounds may be formulated in a variety of ways. The concentration of active compound in the formulation may vary from about 0.01-100 wt. %.

One of the bioelimination routes for the contrast agents of this invention can be renal. The macrostructure is eventually to be abstracted by the RES and it is preferred that chelate attachment should be via biodegradable bonds that on cleavage release fragments that are renally excretable, e.g. with a molecular weight of less than 60 KDa, preferably less than 10 KDa, especially 200 to 5000 Da. To alter the bio-elimination route, a fusion protein or a non-degradable particle moiety can be added to the protein contrast agent.

To overcome immunogenicity, the contrast agent can be modified for use with the specific organism by those with ordinary skill in the art. For example, where the contrast agent in used in rats, the contrast agent may be modified by incorporating the rat self sequence. Further, it is contemplated that the contrast agent could include human sequences. An additional advantage of the protein-based agent of the present invention is that it is relatively easy to target the specific tissues and biomarkers for molecular imaging of tissues and tissue growths such as cancer. The active targeting of contrast agents to specific organs or tissues can be achieved by incorporation of lipids with monoclonal antibodies or antibody fragments that are specific for tumor associated antigens, lectins or peptides attached thereto.

Scaffold Proteins.

Scaffold proteins suitable with the present invention include proteins or organic polymers containing amino acids. Such scaffold proteins are inclusive of both natural amino acids and unnatural amino acids (e.g. beta-alanine, phenylglycine, and homoarginine). While amino acids are alpha-amino acids, which can be either of the L-optical isomer or the D-optical isomer, the D-optical isomers may be preferred, as such isomers are less subject to proteolytic degradation. Such amino acids can be commonly encountered amino acids that are not gene-encoded, although preferred amino acids are those that are encodable.

Various scaffold proteins may be used according to the invention but in general they will be proteins, terminally modified proteins, and organic polymers. More specifically, suitable scaffold proteins can be selected with properties suitable for diagnostic applications. The scaffold protein for use with this invention may be of unitary construction (a particulate, a polychelant or a dendrimeric polymer). Scaffold proteins suitable with this invention may be selected without undue experimentation.

The scaffold protein also can be a natural protein that ordinarily binds a metal ion. In such embodiments, it is possible to modify the natural metal binding sites to chelate heavy metals or paramagnetic metals or other metals useful in diagnostic imaging. For example, it is possible to tailor the amino acid sequence of the scaffold protein that ordinarily binds $Ca^{2+}$ to bind $Gd^{3+}$ by modifying amino acid ligand residues contained therein. For example, one can modify the binding sites in alpha-lactalbumin to bind $Gd^{3+}$ (e.g. as shown in FIG. 3). For another example, it is possible to modify EF-hand calcium binding sites in proteins such as calmodulin to bind $Gd^{3+}$ (e.g. CA9.CD2).

In illustrative embodiments, a scaffold protein can be selected for the following criteria:

1) Exhibition of strong stability in terms of resistance to pH denaturation and resistance to proteolytic cleavage.

2) The availability of structural information about the protein. If less structural information is available, which allows for the rational design of metal binding sites with optimized inner, secondary and outer sphere relaxation and metal binding properties, then structure prediction can allow for the modification of the protein.

3) Tolerance of mutations without sacrificing native conformation and folding.

4) The molecular sizes are suitable for the particular application. An optimal size can be dependant on a particular diagnostic application. For example, a compact structure, e.g. molecular weights between 11-30 KDa, and rotational correlation times of ~10-30 ns. Further, a molecular size can improve circulation retention times and tissue penetration. For example, stronger in vivo kidney images and prolonged retention time can allow for more detailed imaging of the renal system for diagnosing kidney diseases such as renal carcinoma and can allow for more precise measurement of blood flow and volume. Further, a proper size of the protein frame can provide improved tissue penetration and molecular targeting, which can be a limitation of some of the large size of dentrimers, nano-particles, and superparamagnetic particles.

5) Optionally, the scaffold protein also can have intrinsic properties, which can allow for the construction of multifunctional probes and use of fluorescence as a tool to assist in the design of MRI contrast agents for molecular imaging without the need of other fluorophores.

Suitable proteins include proteins from immunoglobulin G (IgG) superfamily such as CD2 proteins (a cell adhesion protein) that exhibit high stability against proteolysis, thermal conditions (Tm 67 C), pH (2-10), and salt (0-4 M NaCl) denaturation. CD2 proteins can be suitable with this invention because such proteins are stable in physiological environments, have a topology suitable for the integration of at least one or multiple metal ion chelating sites, and typically have a relaxivity greater than 10 mM$^{-1}$s$^{-1}$ (some of them up to about 50 mM$^{-1}$s$^{-1}$). In addition, CD2 can tolerate multiple surface mutations without unfolding the protein. Other research has shown that CD2 can be used as a host protein to design calcium binding sites. Examples using CD2 are described below.

Fluorescent proteins are another class of preferred scaffold protein for this invention, as these proteins are stable in a physiological environment against proteolytic degradation and pH denaturation (pH 5-10). Such fluorescent proteins include an array of fluorescent proteins including those related to *Aequorea*. Suitable fluorescent proteins should have a useful excitation and emission spectra and may have been engineered from naturally occurring *Aequorea victoria* green fluorescent proteins (GFPs). Such modified GFPs may have modified nucleic acid and protein sequences and may include elements from other proteins. The cDNA of GFPs may be concatenated with those encoding many other proteins—the resulting chimerics are often fluorescent and retain the biochemical features of the partner proteins. Yellow fluorescent proteins and blue fluorescence proteins and red fluorescent proteins can also be used to as the scaffold proteins for contrast agents. Such proteins also are included in the invention.

Other suitable proteins include extra cellular receptors and growth factors known to be stable against protein cleavage. In addition, proteins from four-helical bundle family (such as Rop), the maltose binding protein family, and thioredoxin family have been shown to accept mutations and metal binding sites. While the inventors have not tested every protein for suitability as a scaffold protein, the diverse array of examined proteins demonstrates this invention includes all of the proteins having the criteria disclosed herein. It is contemplated that one of ordinary skill in the art can develop and select a suitable scaffold protein using ordinary research techniques and the criteria disclosed herein.

One advantage of using fluorescent proteins is that contrast agents constructed from such proteins can be multi-functional probes. In such an embodiment, the contrast agent constructed from fluorescent proteins can be screened using both fluorescence and MR imaging. This can be extremely advantageous as such properties equip the contrast agent with both the fluorescence needed for fluorescence detection methods and the sensitivity needed for the deep tissue detection from MRI. Such contrast agents are multifunctional contrast agents.

Other proteins may be used as scaffold proteins for this invention. Preferably, scaffold proteins are able to tolerate the addition of the metal ion binding site without substantial disruption to its structure. One of ordinary skill in the art can select a scaffold protein based on preferences without undue experimentation.

Metal Ion Binding Sites

The affinity of the metal ion binding site may vary the contrast agent affinity for metal ions. Specifically, as affinity and sensitivity of the metal ion binding sites may be modified, the relaxivity and metal affinity of the contrast agent may be modified. Preferably, the metal ion binding site has optimal imaging properties including metal binding affinity, selectivity, relaxivity, nuclear magnetic relaxation Dispersion (NMRD) profile, and water exchange rates.

One of ordinary skill in the art can use methods known in the art or developed hereafter to develop a metal binding site having optimal characteristics. For example, the metal ion binding site of the present invention can be constructed at least using these methods:

(1) A computational design approach in which the metal ion binding site with a selectivity and affinity for a metal ion is engineered and rationally designed de novo based on optimal binding characteristics of the metal ion with other moieties;

(2) A grafting method in which the metal ion binding site with a selectivity and affinity for a metal ion is engineered and constructed selectively by varying the primary, secondary, tertiary, and/or quaternary structures of an identified binding site; and (3) Other methods known or developed hereafter and a combination of methods known or developed hereafter.

1. The Computational Design Approach

The computational design approach focuses on designing a metal ion binding site de novo. This design approach focuses on using an algorithm to construct and engineer an optimal binding site. Preferably, the computation design approach is used to create optimal binding sites by, e.g., varying the coordination geometry of the site, the water number in the coordination shells, the ligand types, and the charges.

The computational design approach comprises the following steps:

(1) Accessing one or more databases having structural, coordination, and/or 3-dimensional structures or models of metal ion binding sites, or creating model structures based on the sequence homology to other metal binding sites;

(2) Generating one or more preliminary metal ion binding sites from portions of the structural data;

(3) Selecting rationally one or more suitable metal ion binding sites from the generated preliminary binding sites based on, e.g., coordination geometry; and (4) Creating a metal ion binding site by tailoring and tuning the selected metal ion binding site.

The metal ion binding site may be incorporated into a scaffold protein, e.g. a fluorescent or CD2 protein. Further, such a method may be used to alter metal ion binding properties of proteins and generate new materials with various ion binding affinities.

More particularly, the method involves searching and accessing public and or private databases for preferred components of a metal ion binding site. Such databases that may be searched for the criteria or components may include public domain banks (e.g. National Center for Biotechnology Information (NBCI) or PubMed of the US National Institution of Health) or knowledge banks such as protein modeling structure data banks (e.g. Cambridge or RCSB Protein Data Bank Data Bank and BioMagResBank database) or other biotechnological data banks. Further, the database could include structural data from metal ion binding proteins whose structures have been characterized previously. One of ordinary skill in the art can identify databases and sources of material for databases suitable with this invention. Use of a computer with interne or internet capabilities obviously would greatly speed up the searching and is preferred.

These databases may be used to provide structural analysis of one to several thousand different small molecules or metal ions that bind to a protein. Such analysis may include local coordination properties, types of residues or atoms commonly used to bind a desired metal ion, chemical features (e.g. pKa or changes), the number of charged residues on a site, and the range or deviation of the known binding sites. Further, such analysis may include the environment, such as types of atoms, residues, hydrophobicity, solvent accessibility, shapes of the metal binding sites, electrostatic potentials, and the dynamic properties (e.g. B-factors or the order factors of the proteins) of the binding sites. Such analysis also may include whether a binding site for a particular metal ion is a continuous or discontinuous binding site.

Once preliminary metal ion binding sites are found, using the structural data and analysis, one or more suitable metal ion binding sites may be generated based on rational factors. Specifically, different search algorithms may be used to generate potential metal ion binding sites based on other key features in addition to, for example, the geometric descriptors. These key features include the properties of the original residues in the scaffold protein, ligand positions that are essential to protein folding, the number of the charged residues and their arrangement and number of water molecules in the coordination shell. The hydrogen bond network and the electrostatic interactions with the designed ligand residues also can be evaluated. Furthermore, the protein environments of metal ion binding sites can be analyzed according to solvent accessibility, charge distribution, backbone flexibility, and properties of scaffold proteins. Thus, one of ordinary skill in the art may rationally select a binding site based on desired parameters.

Once the metal ion binding sites are generated, a site may be tailored using two complementary approaches of computational design and grafting (see below). First, as discussed above, the metal ion binding site may be tailored using a grafting method in which the primary, secondary, tertiary, and/or quaternary structures are tuned. Second, the metal ion binding site may be tailored using a computational design approach. It is understood that one or both of these approaches may be used to tailor the binding site.

The computational design approach includes modifying the metal ion binding site by modifying residues in the scaffold of the metal ion binding site. In one embodiment, a geometric or statistical description of the ligands around a metal ion, a three-dimensional structure of the backbone of proteins, and a library of side-chain rotamers of amino acids (or atoms from the main chain) can identify a set of potential metal-binding sites using a computer. Using the geometric and graph description of a particular metal ion site, key ligand residues are carefully placed in the amino acid sequence to form the metal (metal ion) binding pocket. This binding pocket can be created automatically by a computer algorithm designed according to the coordination description and the user's preferred affinity.

The created potential metal ion binding sites can be optimized and tuned to specification. A backbone structure of the metal ion binding site with different degrees of flexibility may be used according to the need or the flexibility of the metal ion binding site. The designed metal ion binding sites are further filtered and scored based on the local factors, which may include the shape of the metal ion binding sites, locations, charge numbers, dynamic properties, the number of mutations needed, solvent accessibility, and side chain clashes. To achieve the maximum relaxivity, it can be important to have one to two oxygen atoms from the solvent water molecules in the coordination shell without reducing the required binding affinity and selectivity.

Stronger metal ion binding affinities of the designed sites may be developed based on several modeled factors that contribute to metal ion affinity. For example, the number of ligand residues is a factor to directly chelate a specific metal ion. In some cases, in order to have a strong metal ion affinity with a $K_d$ necessary to measure a metal ion concentration, it is necessary to include residues from the protein frame for optimal metal ion binding. In other cases, the number of charged residues is able to change metal ion affinity. In still other cases, the ligand type is a factor as the binding preferences of a chelate may depend on the particular ligand type. Other factors, such as negatively charged environments, may contribute to the binding affinity of a metal ion binding protein and can be taken into account by those of ordinary skill in the art without undue experimentation. These charged residues can increase the water-exchange rate to avoid its limitation for the required relaxivity.

An illustrative version of this computational approach is the computerized (or otherwise automated) querying of one or more databases that comprise structural data on metal ion binding sites using selected criteria relevant to the metal ion binding site, generating at least one preliminary metal ion binding site from the database information based on compatibility with the selected criteria, and selecting one or more suitable metal ion binding sites from the preliminary metal ion binding sites based on optimal compatibility with the selected criteria. Once a suitable metal ion binding site is selected, the nucleic acid sequence of the selected metal ion binding site is obtained, tailored, and operatively linked with a scaffold protein sequence, whereby the nucleic acid sequence of the selected metal ion binding site is tailored so to achieve the metal ion binding site having a desired specificity for the metal ion. Further, a nucleic acid sequence encoding the preliminary binding sites can be generated from the structural or model data. The computational approach also can be used to produce the metal ion binding site.

The computational approach can be performed on or by a system comprising at least one database that comprises the structural data on metal ion binding sites, an algorithm for generating the preliminary metal ion binding sites from portions of the structural or model data using selected criteria relevant to the metal ion binding site and rating the preliminary metal ion binding sites based on specificity for a selected metal ion, and a computer for executing the algorithm so as to query the databases to generate the preliminary metal ion binding sites. The algorithm generally is a relatively simple searching algorithm that will query the databases based on inputted criteria.

2. The Grafting Method

The grafting method focuses on engineering and constructing a metal ion binding site by modifying the primary, secondary, tertiary, and/or quaternary structure of an identified binding site. By selectively manipulating the structure of the binding site, it is possible to obtain a metal ion binding site that can be engineered into a scaffold protein, e.g. CD2 or fluorescent protein, without significantly denaturing the protein. Using the grafting method, it is possible to achieve a binding site that has a stronger preference for one metal ion over another metal ion. Such modifications may allow for improved contrast abilities.

Initially, an identified binding site for use with the grafting method may be any continuous sequence site that has some affinity for a metal ion. Such binding sites may derive from either known binding peptides such as an individual EF-hand site or from short fragments that have demonstrated the ability to bind specific metal ions such as alpha-lactalbumin. Such peptides may be highly conserved in nature and prevalent throughout nature or may be unnatural but known to have an affinity for a particular metal ion. One of ordinary skill in the art is able to identify binding sites with affinity for a metal ion without undue experimentation. Once the binding site has been identified, the primary structure of the metal ion binding site may be altered and tuned to achieve a metal ion binding site with improved binding characteristics. For example, more charged ligand residues such as aspartate and glutamate may be engineered by inserting codon(s) into the metal ion binding site so as to tune the responsiveness of the site or the scaffold protein. The inclusion of additional charged ligands can allow the contrast agent to achieve an affinity for selected paramagnetic metal ions and to have a desired selectivity. Additionally, one or two water molecules can also be introduced into the coordination shell by removing or modifying ligand residues and their environments. Further, other mutations to the primary structure include removing or adding amino acids to change properties such as flexibility or rigidity of the site. Adding or removing amino acids from the binding site alters the primary structure of the binding site.

The secondary structure of the metal ion binding site, that is, the spatial arrangement of amino acids residues that are near one another in linear sequence, may be modified to tune the sensitivity and responsiveness of the metal ion binding site. The residues on the site itself, the flanking or the neighboring structures such as helices, beta strands, or turns may be modified by changing properties such as hydrophobicity, salt bridges, secondary structure propensity (e.g. helicity, and β-sheets), and charge interactions with different amino acids, which all may inherently change the secondary structure.

The tertiary structure of the metal ion binding site may be modified to further tune the sensitivity and responsiveness of the metal ion binding site. The affinity of the metal ion binding site for the metal ion may be varied by selectively manipulating and adding helices, loops, bridges and/or linkers and chemical properties such as hydrogen bonding, electrostatic interactions and hydrophobic interactions. In fact, such variations in tertiary structure may add stability and affinity by increasing secondary structure propensity, adding charge interaction of the side chains, and by stabilizing the metal ion binding coordination chemistry. As such, it may be possible to increase or decrease the binding affinity of the continuous binding site by tuning the tertiary structure of the metal ion binding site. In addition, the dynamic properties can be modified by increasing the packing of the protein and replacing residues with amino acids or other moieties with more rigid (e.g. Pro) or flexible (e.g. Gly) properties, or adding disulfide bonds.

One method of directly altering the primary, secondary, and/or tertiary structure of the metal ion binding site is by altering the charges in the site. As the charges in any binding site have a significant role in the structure of the site, changing the charges or charge ratio may have significant impact on the structure of the site. More importantly, as the charged side chains exhibit a strong influence on the metal ion binding affinity even though they are not directly involved as ligands, the variation of these chains results in variations in metal ion binding affinities and selectivity. A metal ion binding site may have stronger affinities to and better selectivity for a desired metal ion over a competitive metal ion by designing or modifying the site, e.g., changing the number of charged ligand residues to form metal ion binding pockets. For example, the metal ion binding affinity of the metal ion binding site may be varied by changing the charged side chains that are present on the metal ion binding site and or the neighboring environment. The replacement of charged residues such as aspartate or glutamate with a residue such as alanine may dramatically reduce the binding affinity for the metal ion by up to 100 times.

In the case of multifunctional contrast agents, e.g. where the contrast agent is a fluorescent protein, it can be important to induce metal binding sites without altering significantly the chromophore environment to reduce the fluorescent/optical signal. These metal binding sites can be added at remote locations away from the chromophore or simple fusion to the fluorescent moieties. Such locations can be evident from the sequence and protein folding.

In other embodiments, the grafting approach may be used with the design approach to create optimal metal binding sites. For example, metal binding sites can be created by using part of a continuous binding site and part of ligand residues created by computer design. The loops or any sequences of the proteins can be removed or modified to achieve optimal required binding affinity, metal selectivity, relaxivity and stability. Thus, by varying the primary, secondary, and/or tertiary structure of the metal ion binding site, it is possible to achieve a metal ion binding site with desired specificity and affinity and more importantly contrast abilities.

3. Other Methods

The metal ion chelating or binding can be developed using methods known or developed hereafter. Such methods include protein engineering methods that are readily available in the art, which include by modifying the existing metal binding sites to change the metal binding specificity and dynamic properties. Such methods also include techniques to modify existing binding sites with protein ligand residues or fuse to protein-contrast agents with other molecules, which include the formation of metal binding sites with other molecules/prosthetic groups including non-natural amino acids or carbohydrates or phosphates. Exemplary methods for protein engineering or for design suitable methods are also disclosed in Barondeau D. P. and Getzoff E. D., Structural Insights into Protein-Metal Ion Partnerships, Current Opinion in Chemical Biology, 2004, 14:7; and Lu, Y, Design and Engineering of Metalloproteins Containing Unnatural Amino Acids or Non-Native Metal-Containing Cofactors, Current Opinion in Chemical Biology, 2005, both of which are incorporated by reference in their entirety.

Further, it is possible to combine methods to prepare desired metal ion chelating sites.

Selecting Metal Ion Binding Sites in the Scaffold Protein

The metal ion binding sites may be selectively introduced into numerous sites of a scaffold protein without substantially impairing its secondary structure. A number of methods for identifying integration sites in proteins, such CD2 proteins, fluorescent proteins (e.g. GFP, YFP, CFP, and RFP) are known in the art, including, for example, site directed mutagenesis, insertional mutagenesis, and deletional mutagenesis. Other methods, including the one exemplified below and in the Examples, are known or easily ascertained by one skilled in art.

The sites of the fluorescent protein that can tolerate the insertion of a metal ion binding site also may be determined and identified by gene manipulation and screening. By generating mutant proteins and by manipulating the DNA sequence, it is possible to obtain a variety of different insertions, which then may be screened to determine whether the protein maintains its intrinsic activities. Preferably, sites that remove or interfere with the intrinsic fluorescence of the fluorescent protein are not optimal and may be screened out. Variants identified in this fashion reveal sites that can tolerate insertions while retaining fluorescence.

The preferred metal ion binding sites for use with scaffold proteins may be selected by considering five criteria so as to optimize the local properties of the metal binding site, the fluorescent protein, and the protein environment. First, the geometry of the metal ion binding site should have relatively minor deviations from the desired coordination geometry. Second, negatively charged residues should be varied by no more than 3-5 charges according to the desired affinity for metal ion ($K_d$). Third, the water coordination shell of the metal ion chelating sites should be able to coordinate at least 1-2 water molecules. Fourth, the residues from the loops between the secondary structures with good solvent accessibility are desired for both the folding of the protein and the fast kinetics required for the contrast agent.

The mutation or the introduction of the metal ion binding site should not substantially interfere with the synthesis and folding of the protein. More particularly, the introduction of the metal ion binding site should not interfere with either post-translational chromophore formation or intermolecular interactions required for stabilizing the chromophores and folding of the protein frame. Furthermore, the introduced side chain should not be overpacked and should not clash with the protein frame of the scaffold protein (e.g. the fluorescent protein). The direct use of chromophore residues as chelating sites is not preferred but is within the scope of this invention.

Metal Ions

Metal ions are atoms and ions, including the respective isotopes and radioisotopes, that can bind to proteins or peptides. A metal ion may bind reversibly or irreversibly and such a bond may be covalent or non-covalent. While $Gd^{3+}$ is used in preferred embodiments of this invention as an exemplary metal ion for MRI contrast agents, it is understood that metal ions suitable with this invention include, but are not limited to metal ions including paramagnetic metal ions, transition metal ions, and Lanthanide Series ions. Exemplary metal ions include, but are not limited to, the ion, isotope, and/or radioisotope forms of magnesium, calcium, scandium, titanium, manganese, iron, boron, chromium, cobalt, nickel, cooper, zinc, gallium, strontium, yttrium, strontium, technetium, ruthenium, indium, hafnium, tungsten, rhenium, osmium, and bismuth. It is also possible to use radioisotopes of metals with this invention. Paramagnetic metal ions are the preferred metal ions for use with this invention.

The metal ions chosen to be chelated by the contrast agents depend in part on the diagnostic role of the ion. Metals that can be incorporated, e.g. through chelation, include lanthanides and other metal ions, including isotopes and radioisotopes thereof. For MR imaging applications, the preferred metal ion is a paramagnetic metal ion such as gadolinium. One of ordinary skill in the art can select a metal ion for chelation, based on the intended diagnostic application, without undue experimentation.

As mentioned, the choice of metal ions to be held in chelate complexes by the contrast agents of the invention depends upon the diagnostic technique for which the agent is to be used. For MRI or MRS or EPR applications, the metal ions should be paramagnetic (metal ions with unpaired electrons), and preferably non-radioactive. For X-ray and ultrasound imaging, heavy metal ions, e.g. with atomic numbers of at least 37, preferably at least 50, should be used, again preferably non-radioactive species. For scintigraphy the metal ions should be ions of radioactive isotopes. For MR, X-ray, EIT or magnetometric imaging, one may use chelating groups to bind to heavy metal clusters (e.g. polyoxoanions and full or partial sulfur analogues) or to iron oxides or other superparamagnetic polyatomic species.

Methods of complexing metal ions with chelants and polychelants are known to those with ordinary skill in the art. Metal may be incorporated into contrast agent, i.e. the tailored binding sites, by direct incorporation, template synthesis, and transmetallation. Preferably, the metal ion is chelated into the contrast by direct incorporation, which involves titration with solution of sub-stoichiometric levels up to full incorporation.

EXAMPLES

In following examples, the inventors have focused on disparate proteins, namely, immunoglobulin super-family proteins and fluorescent proteins. For example, domain 1 of the cell adhesion protein CD2 and the green fluorescent protein were selected as scaffold proteins (e.g. FIGS. 1A and 1B) for the integration of engineered various metal (e.g. $Gd^{3+}$) binding sites for several reasons. Further, the 3D model structures of 6D79 of CD2 variant with designed metal binding sites (ball) and the model structures of 6D79 and 7E15 based on doamin1 of rat CD2 (1hng). 3D structure of GFP (1b9c) with designed $Gd^{3+}$ sites and the chromophore highlighted. The $Gd^{3+}$-binding residues and the adjacent residues are shown. The residues close to strand B also are represented in the figure. For example, FIG. 1A shows a 3D structure of CD2 with designed metal binding site. The loops that undergo relatively large dynamic property changes are shown in orange. Only one residue is labeled when continuous residues are colored.

First, these proteins exhibit strong stability in terms of resistance to pH denaturation and resistance to proteolytic cleavage. For example, the prior art has shown that GFP is extremely stable and cannot be cleaved by proteases such as trypsin, chymotrypsin and thrombin. Further, pervious research has shown that domain 1 of CD2 maintains its native conformation between pH 2 to 11.

Second, various structural information about CD2 and GFP is available, which allows for the rational design of metal binding sites with optimized inner, secondary and outer sphere relaxation and metal binding properties.

Third, these proteins tolerate mutations without sacrificing their native conformation and folding.

Fourth, these proteins have a compact structure, molecular weights between 11-30 KDa, and rotational correlation times of ~10-30 ns. These proteins have been matched to the optimal relaxivity for the current clinically allowed magnetic field strength.

Fifth, the molecular sizes are suitable for good circulation and tissue penetration.

Sixth, in the case of GFP, the intrinsic fluorescence allows for the construction of multifunctional probes and the use of fluorescence as a tool to assist in the design of MRI contrast agents for molecular imaging without the need of other fluorophores.

FIG. 2 shows an example of this methodology in which several $Gd^{3+}$ binding sites were designed at different locations of CD2. $Gd^{3+}$, $Tb^{3+}$, $La^{3+}$ and the other lanthanide metal ions have coordination properties similar to those of $Ca^{2+}$. In the schematic representation of a $Gd^{3+}$ chelate with one inner-sphere water molecules surrounded by bulk water molecule, $\tau_R$ refers to the rotational correlation time of the molecule, $k_{ex}$ to the water/proton exchange rate or the reciprocal of residence lifetime of the coordinated water $\tau_M$ and $1/T_{1,2e}$ to the relaxation rate of $Gd^{3+}$ electron spin. All have a strong preference for oxygen atoms from carboxyl sidechains of Asp, Glu, Asn, and Gln. Small chelators chelates usually have 8 and 7 coordinating oxygen atoms for $Gd^{3+}$ and $Ca^{2+}$, respectively.

For macromolecules such as proteins, the coordination numbers are slightly smaller possibly due to steric crowding effect. The average values for $Gd^{3+}$ and $Ca^{2+}$ are 7.2 and 6.5, respectively. The pentagonal bipyramidal geometry and potential metal binding ligand residues were used in creating metal binding site in CD2 with computer algorithm based on parameters selected by the inventor. As $Gd^{3+}$ is highly positively charged, more negatively charged residues were placed in the coordination shell to increase the affinity for $Gd^{3+}$ over $Ca^{2+}$. Metal binding sites with different numbers of coordination waters (q=1 and 2) have been designed in CD2 (denoted as CA.CD2). For example, CA1.CD2 (see below), the metal binding ligand residues are from different locations of the protein to form a metal binding pocket (discontinuous) while CA9.CD2 (see below) contains a the metal bind site formed by a continuous EF-hand loop from calmodulin linked by a flexible glycine linker. This site is designed to mimic previously reported highly flexible contrast agent conjugated to macromolecule and to test our hypothesis.

The amino acid sequences of exemplary contrast are shown in Sequence Id. Nos. 1 through 19.

The Computational Method for the Design of De Novo Binding Sites in Proteins

The computation method can be used to designed metal binding sites into scaffold proteins. For example, previously published research by the inventor described established parameters such as the pentagonal bipyramidal geometry of the most popular $Ca^{2+}$ binding sites with potential ligand residues such as the carboxyl groups of D, N, E, Q and/or mainchain carbonyl oxygen atoms. The resulting protein preferentially binds $Ca^{2+}$ over $Mg^{2+}$ (10 mM) and $K^+$ (150 mM) at physiological conditions.

These experiments resulted in metalloprotein designs that have a high coordination number (seven) metal binding site constructed into a β-sheet protein. $Gd^{3+}$ and $Ca^{2+}$ share similar coordination geometry and properties. To design de novo $Gd^{3+}$ binding sites into proteins, the inventors started by carrying out detailed structural analysis of $Gd^{3+}$ binding sites in small chelators and proteins.

As shown in FIGS. 1A, 1B and 1C (CD2 derivative), the inventors have solved the NMR structure for one of the designed metal binding proteins. Structural studies revealed that the coordination geometry in the designed proteins is the same as the designed structure. The structural profiles can assist in further designing of $Gd^{3+}$ binding proteins. $Gd^{3+}$ binding proteins also can be designed using developed computational methods.

$Gd^{3+}$ Binding Proteins Can Be Designed with Knowledge About $Ca^{2+}$-Binding Proteins $Gd^{3+}$ binding proteins can be designed using developed computational methods. Since $Gd^{3+}$ has a high number of positive charges, more charged residues in the coordination shell increased the selectivity for $Gd^{3+}$ over $Ca^{2+}$. To systematically evaluate the key factors for the metal selectivity, CD2 variants were created with different numbers of charged ligand residues (2 to 5) in the metal coordination shell. Metal-binding sites with a higher number of negatively charged residues have stronger affinities for $Gd^{3+}$ and $Tb^{3+}$ over calcium. The resulting protein selectively binds $Gd^{3+}$ over $Ca^{2+}$ at physiological conditions with $K_d$ values for $Gd^{3+}$ and $Tb^{3+}$ <0.01 μM and for calcium >50 μM.

The inventors have designed $Gd^{3+}$ binding sites in GFP in a pentagonal bipyramidal geometry with seven ligands using established computer algorithms. Several of the designed sites at different locations in GFP are shown in FIG. 1C. GFP variants with designed metal binding sites exhibit strong metal binding affinity for the $Gd^{3+}$ analog $Tb^{3+}$. This demonstrates that a general method for designing metal binding sites has been developed.

Affinity and Selectivity of Metal Binding As $Tb^{3+}$ has an ionic size similar to $Gd^{3+}$, the developed $Tb^{3+}$ sensitized fluorescence resonance energy transfer (FRET) method may be used to measure the binding of $Gd^{3+}$. See Ye Y., et al. Metal Binding Affinity and Structural Properties of an Isolated EF-Loop in a Scaffold Protein, *Protein Eng*, 14, 1001-13 (2001). This method can obtain the lower limit of metal binding affinities. The addition of $Gd^{3+}$ competes for the $Tb^{3+}$ binding pocket and shows a decrease in $Tb^{3+}$ FRET enhancement. Therefore, the $Gd^{3+}$ binding affinity can be estimated. To accurately measure metal affinity compared with the known stability constant of (ethylenedioxy)diethylene nitrilotetraacetate (EGTA), the inventors have obtained the relative binding constant of EGTA for $Tb^{3+}$ using the $Tb^{3+}$ FRET method under the same experimental conditions. Therefore, the stability of designed contrast agents can be accurately obtained.

Designed Contrast Agents Exhibit High MRI Proton Relaxivity

In the designing of preferred contrast agents, the following factors were considered:

1) A high relaxivity, especially for T1, in order to obtain better images.

2) A specific in vivo distribution providing molecular imaging of desired targets.

3) The toxicity (negligible or low) of a metal-loaded contrast agent is a prerequisite as free $Gd^{3+}$ is toxic. The contrast agent should be thermodynamically and kinetically stable, e.g. with high binding affinity and very low off-rate, which can minimize the release of free toxic $Gd^{3+}$. A contrast agent with high relaxivity and the capability to target specific tissues or organs dramatically reduces its required concentration for imaging and toxicity. In addition, a $Gd^{3+}$-loaded contrast agent does not compete with the proteins for metal binding.

4) The solubility and excretion time of the agents from the body to allow imaging and reduce toxicity. Directly coordinating $Gd^{3+}$ ions by protein ligand residues eliminates the high internal mobility of the paramagnetic moiety associated with polymers and protein conjugates.

Relaxation times, T1 and T2, were determined at 3 Tesla. T1 was determined using inversion recovery and T2 using a multi-echo Carr-Purcell-Meiboom-Gill (CPMG) sequence. Samples were imaged and relaxation parameters calculated prior to $Gd^{3+}$-binding and after adding $Gd^{3+}$ in 1:1 molar ratio. As shown in Table 1 (below), the designed contrast agent CA1.CD2—exhibits T1 relaxivity up to 48 $mM^{-1} s^{-1}$, about a 10-fold increase in the sensitivity compared to that of DTPA. A concentration of 50 μM, contrast agent CA1.CD2 is able to generate a bright image while Gd-DTPA could not produce a visible image. This suggests that a significantly lower local concentration (~10 μM) is enough for good imaging. In addition, several other designed CD2 variants such as CA3.CD2-6D79 and EEDDN also exhibit relaxivity values >30 $mM^{-1} s^{-1}$. On the other hand, CD2 with grafted EF-loop III modified from calmodulin (CA9.CD2) is similar in relaxivity to DTPA, possibly due to the intrinsic mobility of the metal binding site.

TABLE 1

T1 proton relaxivity of different classes of contrast agents

| Type | Compounds | $T_1$ relaxivity ($mM^{-1} s^{-1}$) | Number of metal | Magnetic field Bo(T) | MW (KDa) |
|---|---|---|---|---|---|
| *Small compound | GdDTPA | 4.5 | 1 | 1.5 | 0.743 |
| Designed Contrast Agents | | | | | |
| Sequence ID No. 1 | CA0.lac | 4.2 | 1 | 3 | 14.5 |
| Sequence ID. No. 2 | CA1.CD2** | 48 | 1 | 3 | 12 |
| Sequence ID. No. 3 | CA1.CD2-EEDDE | 37 | 1 | 3 | 12 |
| Sequence ID. No. 4 | CA1.CD2-EEDDN | 36 | 1 | 3 | 12 |
| Sequence ID. No. 5 | CA1.CD2-EEDDQ | 14 | 1 | 3 | 12 |

TABLE 1-continued

T1 proton relaxivity of different classes of contrast agents

| Type | Compounds | $T_1$ relaxivity $(mM^{-1} s^{-1})$ | Number of metal | Magnetic field Bo(T) | MW (KDa) |
|---|---|---|---|---|---|
| Sequence ID. No. 6 | CA1.CD2-NENDN | 9 | 1 | 3 | 12 |
| Sequence ID. No. 7 | CA1.CD2-EENDN | 34 | 1 | 3 | 12 |
| Sequence ID. No. 8 | CA2.CD2-6D31 | 34 | 1 | 3 | 12 |
| Sequence ID. No. 9 | CA2.CD2-R31K | 37 | 1 | 3 | 12 |
| Sequence ID. No. 10 | CA3.CD2-6D79 | 35 | 1 | 3 | 12 |
| Sequence ID. No. 11 | CA9.CD2 | 5 | 1 | 3 | 12 |

*From reference.

The proton relaxivities of designed proteins are not altered in the presence of excess $Ca^{2+}$ and a strong natural $Ca^{2+}$ binding protein does not have an enhanced proton relaxivity. In order to assess the stability of $Gd^{3+}$ binding under conditions mimicking the extracellular environment and other biological metal ions on the relaxivities of the designed $Gd^{3+}$ binding proteins, the T1 parameter was measured in the presence of 1:1 or 100:1 ratio of $Ca^{2+}$ over $Gd^{3+}$ (up to 10 mM $Ca^{2+}$). The results in Table 1 show that the relaxivities of the instant developed contrast agents were not significantly affected in the presence of 100 fold excess $Ca^{2+}$.

The relaxivity of these designed contrast agents were further measured with tissues from different organs and serum of mice for more than two days. No significant change of relaxivity values were observed, further suggesting those pure designed contrast agents have in vivo stability.

Figure 3A:
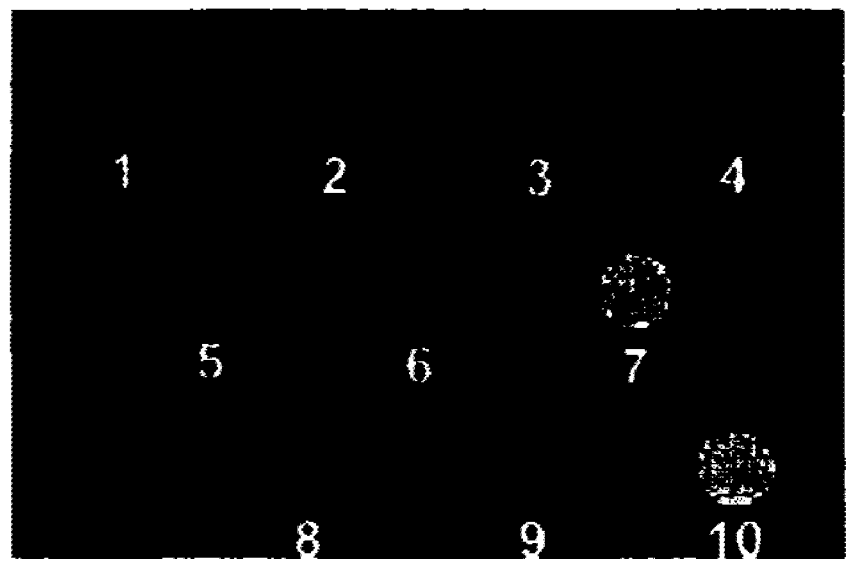
FIG. 3A shows MR images produced by various contrast agents and DTPA.
Figure 3B:
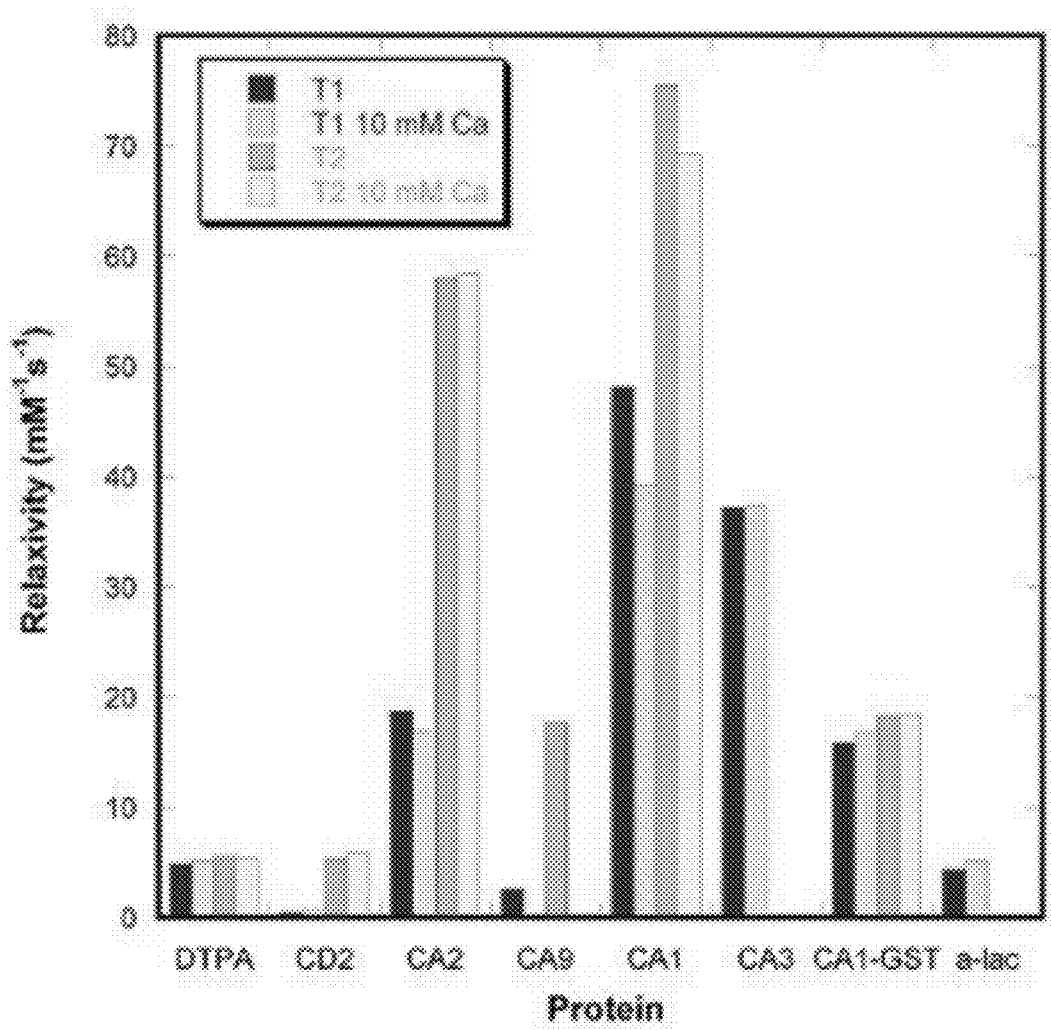
FIG. 3B shows the proton relaxivity of different contrast agents compared to DTPA.

Samples were imaged and relaxation parameters calculated prior to and after adding $Gd^{3+}$ in 1:1 molar ratio. FIG. 3A shows the sample order from top row left to right, then second row, left to right, then third row left to right is: 1) dH2O, 2) Iris, 3) Gd-DTPA in $H_2O$, 0.10 mM $Gd^{3+}$, 4) Gd-DTPA in Tris, 0.10 mM $Gd^{3+}$, 5) 0.092 mM $Gd^{3+}$-w.t.CD2, 6) 0.077 mM $Gd^{3+}$-CA4.CD2, 7) 0.10 mM $Gd^{3+}$-CA2.6D31, 8) 0.10 mM $Gd^{3+}$- CA9.CD2, 9) 0.020 mM $Gd^{3+}$-CA1.CD2-GST, and 10) 0.050 mM $Gd^{3+}$-CA1.CD2. FIG. 3B shows MR images produced using Spin-echo sequence, TR 6000 ms, TI 960 ms, TE 7.6 ms at 3T. These results demonstrate success in creating $Gd^{3+}$ binding sites in scaffold proteins, which can preferentially bind $Gd^{3+}$.

Correlation Time of Designed Metal Binding Proteins

Figure 4A:
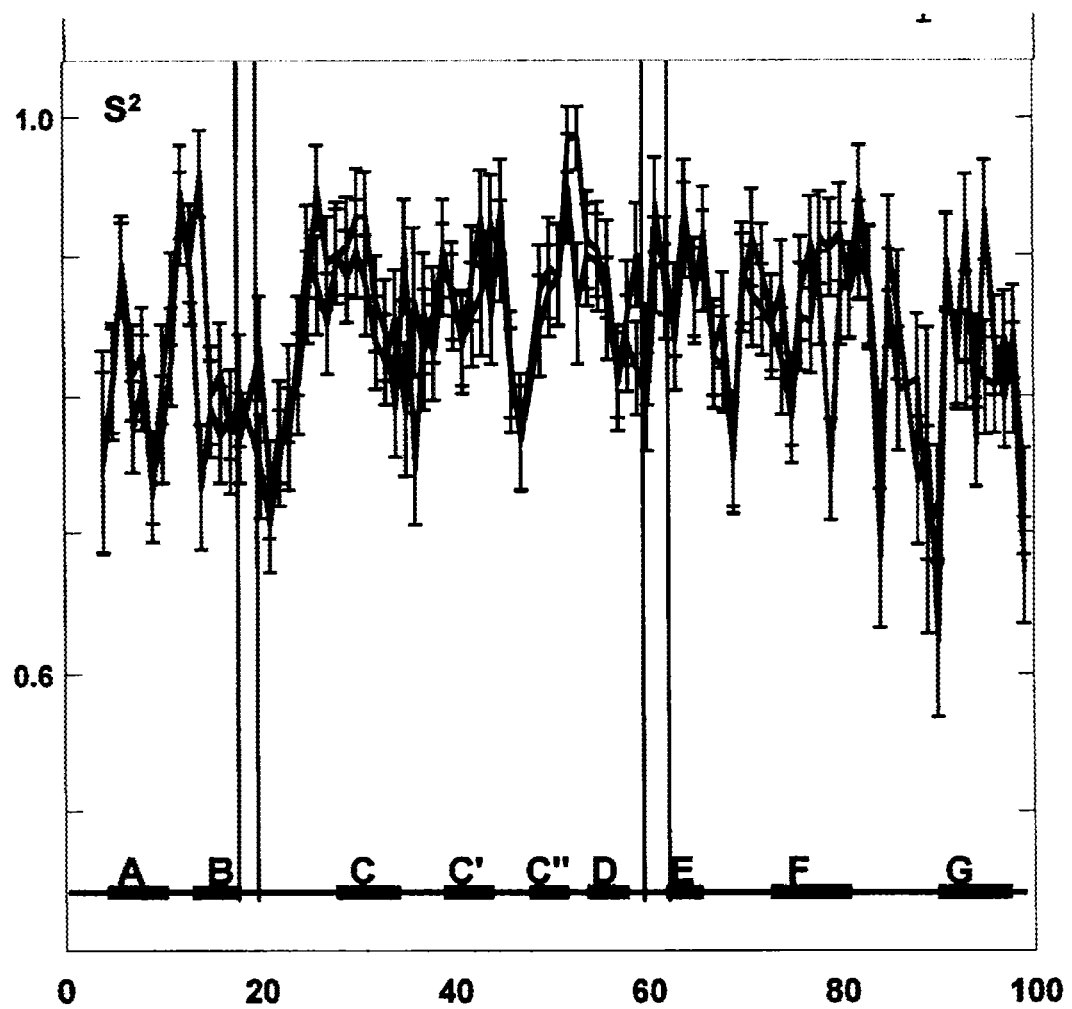
FIG. 4A shows the dynamic properties of an engineered metal binding protein with discontinuous ligand residues.
Figure 4B:
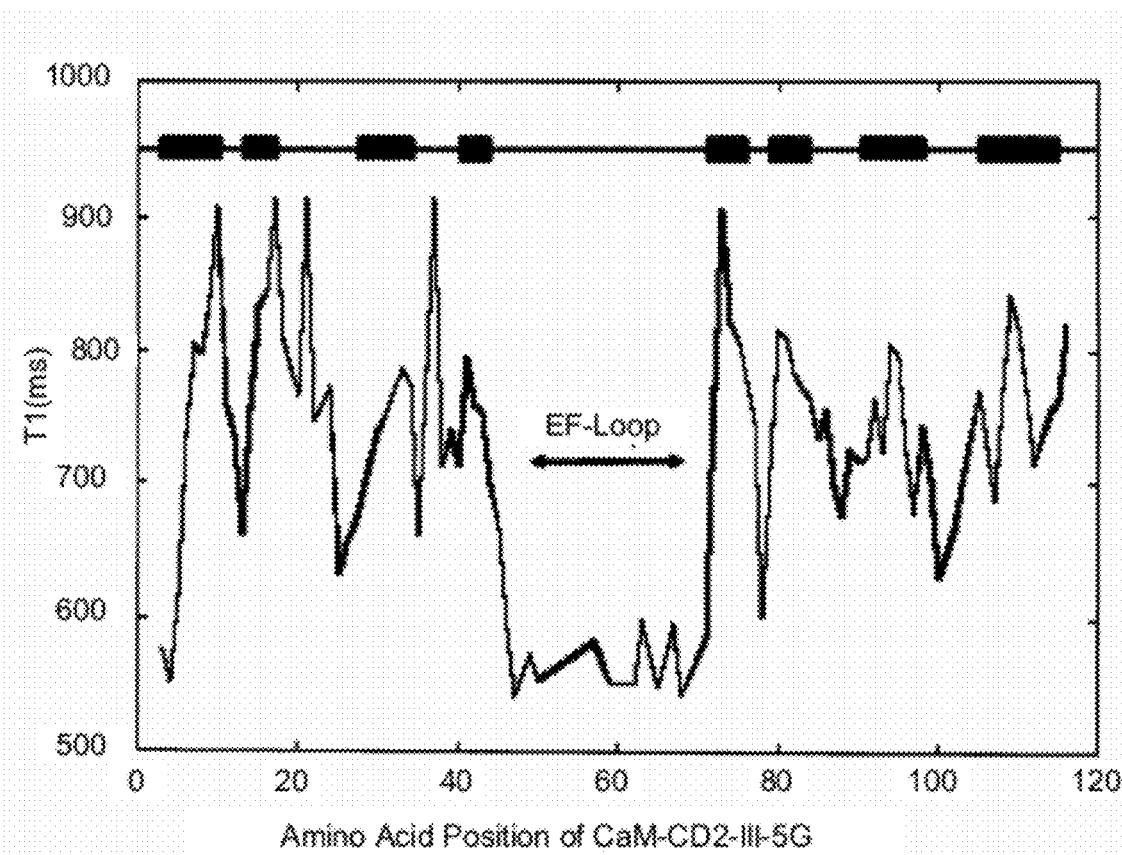
FIG. 4B shows the dynamic properties (T1 time) of CA1-CD2 with a continuous metal binding site.

The inventors also have applied high resolution NMR to probe the dynamic properties of designed metal binding proteins. FIG. 4A shows the dynamic properties of two engineered metal binding proteins. FIG. 4B shows the order factors of CA1-CD2 with discontinuous ligand residues that have the same dynamic properties as the scaffold protein. The T1 values of CA9.CD2 with a continuous metal binding sites linked by a flexible Gly linker. The metal binding site has significantly higher flexibility than the scaffold protein due to the flexible linkers.

The overall correlation time of the designed metal binding protein is 9.2 ns, consistent with proteins of similar size. The order factor $S^2$ of the ligand residues is similar to that of the average value of the protein, suggesting that the metal binding pocket tumbles as a whole with the protein. Therefore, the measured correlation time of the protein directly reflects the $\tau_R$ of the metal binding site. On the other hand, CD2 with the grafted EF-loop III of calmodulin appears to be more flexible than the host protein. Taken together, these results show that designed metal binding sites in proteins with minimized mobility can increase proton relaxivity.

Serum Stability of Designed Contrast Agents

The serum stability of designed proteins were studied by incubating the designed proteins that complex with equal molar of $GdCl_3$ with human serum. The relaxivities of exemplary contrast agents remained intact in the presence of human serum and were not significantly affected in the presence of 100 fold excess $Ca^{2+}$. Further, these designed contrast agents remained intact after incubation in human serum for greater 48 hours.

Developing Protein-Based Contrast Agents by Design

According to the theory developed by Blombergen, Solomon, and others and these results, water q in the coordination shell, $\tau_R$ rotational correlation time, and water exchange rates are the key factors of proton relaxivity. An established design approach to designing additional $Gd^{3+}$ binding sites in domain 1 of CD2 and GFP can optimize the following factors to achieve even higher MRI relaxation signals.

1) Vary coordination geometry: $Gd^{3+}$ is expected to have one or two more coordinated oxygen ligands than $Ca^{2+}$. It has been shown that designed metal binding sites with pentagonal bipyramidal geometry and four to five negatively charged ligand residues are able to bind $Gd^{3+}$ strongly and with good selectivity to $Ca^{2+}$ and $Mg^{2+}$. To test whether increasing ligand atoms can increase metal binding affinity and selectivity, the metal binding sites in the scaffold proteins can be designed by varying the coordination geometries with a total of 6 to 8 ligand residues as shown in Table 2.

TABLE 2

Designed metal binding sites with different coordination numbers from proteins and water

| Total ligand numbers | $1H_2O$ | $2H_2O$ | $3H_2O$ |
|---|---|---|---|
| 7 | 6 p | 5 p | 4 p |
| 8 | 7 p | 6 p | 5 p |
| 9 | 8 p | 7 p | 6 p |

2) Vary water number q in the coordination shell: Increasing the number of water molecules in the coordination shell increases the relaxivity while the metal binding affinity and selectivity might be compromised. Metal binding sites with one to three hydrated water oxygen atoms in the coordination shells with total coordination numbers of 7-9 have been designed (Table 3) to test if the maximum proton relaxivity can be achieved with two coordination water atoms without trading the metal binding affinity and selectivity.

3) Vary ligand types and number of charged ligand residues: As $Gd^{3+}$ prefers more negatively charged ligands than $Ca^{2+}$, a total of 2 to 6 negatively charged ligand residues are designed by varying the number of Asp or Glu as ligand residues as shown in FIG. 3 for site 7E15. Enriched negative charges are expected to enhance the $Gd^{3+}$-binding affinity and stability. It may also increase the relaxivity by facilitating the inner-outer water exchange.

4) Vary the locations of metal binding sites: A good choice of metal binding site locations is essential not only for the protein folding and stability, but also for the proton relaxivity due to the effect of protein environment on the secondary and outer sphere water exchange properties. Table 3 lists the designed metal binding sites at different locations of CD2.

TABLE 3

Designed metal binding sites in CD2

| Designed site | Ligand residues |
| --- | --- |
| CD2-6D15 (CA4.CD2) | N15D, N17D, N60, D62 |
| CD2-7E15 (CA1.CD2) | N15E, L58E, K64D, E56, D62 |
| CD2-6D79 (CA3.CD2) | A92E, T79D, N77, E33, N90 |
| CD2-6D31(CA2.CD2) | R31D, K43D, E29, E41 |

Several locations in both CD2 and GFP were selected based on the following considerations (FIGS. 1A through 1E). First, these protein variants exhibit native like structure and folding properties. In addition, the fluorescence properties of GFP are not altered. Furthermore, the removal of the key residues involved in the binding to CD48 by mutation does not alter the structure of the proteins. The cell adhesion function of CD2 is eliminated to allow CD2 to function solely as a protein contrast agent. Second, all of these metal-binding sites bind to $Gd^{3+}$ analog $Tb^{3+}$ as revealed by $Tb^{3+}$ fluorescence energy transfer. Third, these metal binding sites have different secondary structure and solvent accessibility, which allows testing whether the secondary and outer sphere environment contribute to the water relaxation and metal binding affinity. As shown in FIGS. 1A,1B and 1C, metal binding site (e.g. CA1.CD27E15) is formed by two residues in the beta strand B and three ligand residues from the loop regions while all of the protein ligand residues of 6D79 are from the beta strands.

5) Vary the number of $Gd^{3+}$ binding sites: As the quality of MR imaging is related to the relaxivity and concentration of the contrast agents, multiple sites will be engineered in a single polypeptide chain with the aim of increasing the local $Gd^{3+}$ concentration without changing the protein concentration. The designed $Gd^{3+}$-binding sites using non-overlapped ligands can be tested individually first and then engineered into a single protein. For example, it is possible to create a CD2 with all three $Gd^{3+}$ binding sites of 7E15 (CA1.CD2), 6D79 (CA2.CD2), and 6D31 (CA2.CD2). Similar approaches are used for GFP. Additional metal binding sites can be created by linking the tandem repeats of CD2 and GFP with multiple metal binding sites. As shown in FIG. 1E, multifunctional contrast agents with high payload can be created as CD2-GFP fusion proteins with multiple $Gd^{3+}$ binding sites.

6) Vary the size of proteins: The size of the developed protein has several effects on the properties of the contrast agents. According to the present invention and as pointed out by Lauffer, the correlation time to achieve optimal relaxivity under current clinical magnetic field strength is 10-50 ns, which correlates to the protein with compact structure of 10-30 KDa. Proteins with different domains might have additional internal motions between domains. In addition, the biodistribution and circulation of contrast agents are also dependent on the size of proteins. It is known that proteins with molecular weights in the region of 10-60 KDa have been shown to be ideal for molecular recognition and fast blood diffusion and excretion via the kidney.

Using the methods disclosed herein, the inventors have designed metal binding sites in proteins such as domain 1 of CD2 (11 KDa), CD2-CD2 tandem fusion proteins, GFP (28 KDa), CD2-GST fusion protein (38 KDa), CD2 and GFP fusion proteins (40 KDa) with different molecular weights. These designs allow the development of contrast agents with high relaxivity optimized to the magnetic field strength, and biodistribution and bioelimination. In addition, $Gd^{3+}$ binding sites embedded into stable proteins eliminate the high internal mobility of the paramagnetic moiety and optimal total correlation time and water exchange rates. Furthermore, these tandem repeats of CD2 and GFP containing multiple metal binding sites achieve high payload agents with extremely high sensitivity and reduce the use of the amount of contrast agents and hence significantly reduce the toxicity is also significantly reduced.

Multi-Functionally Targeted Contrast Agents

Multi-functional contrast agents with both the capability for MR imaging and fluorescence optical imaging have been created. See, e.g. FIG. 1D. Fluorescence imaging can be utilized due to its characteristic high sensitivity. See, e.g., Sequence Id. Nos. 16 through 19. Proteins with both paramagnetic binding sites and fluorescence properties have been generated by designing $Gd^{3+}$ binding sites directly in GFP. Studies allow a direct comparison of the results from scintillography and PET, providing spatial information for the cause of the cancer and the progress of the treatment.

Live Imaging

Figures 5A, 5B, 5C, 5D:
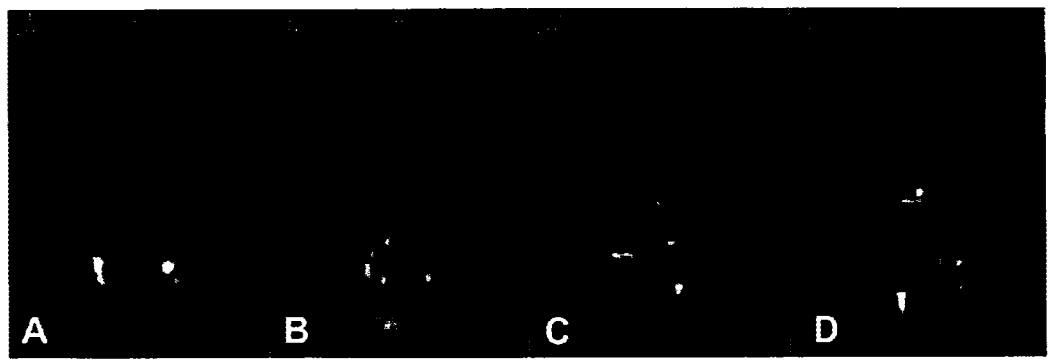
FIG. 5A is a diagnostic image of a mouse prior to being administered an exemplary contrast agent according to this invention.
FIG. 5B is another diagnostic image of a mouse that has been administered an exemplary contrast agent according to this invention.
FIG. 5C is another diagnostic image of a mouse that has been administered an exemplary contrast agent according to this invention.
FIG. 5D is another diagnostic image of a mouse that has been administered an exemplary contrast agent according to this invention.

The distribution of $Gd^{3+}$ in different organs of CD-1 mice was analyzed using ICP-MS for Gd and immunological methods by employing antibodies against the host protein CD2. Critical organs were collected and analyzed. As shown in FIGS. 5A-D, which are chronological images, the immunohistochemical staining studies further revealed that the designed protein mainly localized to the cortex of the kidney, which is consistent with a relatively strong MR image enhancement after administration of the prepared contrast agent. After injection of the contrast agents the animal remained alive and exhibited normal behavior for >5 days. See. FIG. 5B and FIG. 5D, respectively. The organ distributions of the protein contrast agent were further verified by immunohistochemical staining with kidney, liver, and lung tissues.

The in vivo T1 and T2 relaxivity values for Gd-CA1.CD2 in kidney are 49 and 56.8 $mM^{-1}s^{-1}$ kg tissue, which are significantly greater than those reported values for Gd-DTPA in kidney (1.0 and 10.8 $mM^{-1}s^{-1}$ kg tissue, respectively) These results are consistent with the in vitro relaxivity measured using purified protein. The in vivo R2 relaxivity in kidney is about 11.6 fold greater than R1 relaxivity.

Toxicity

Figure 6:
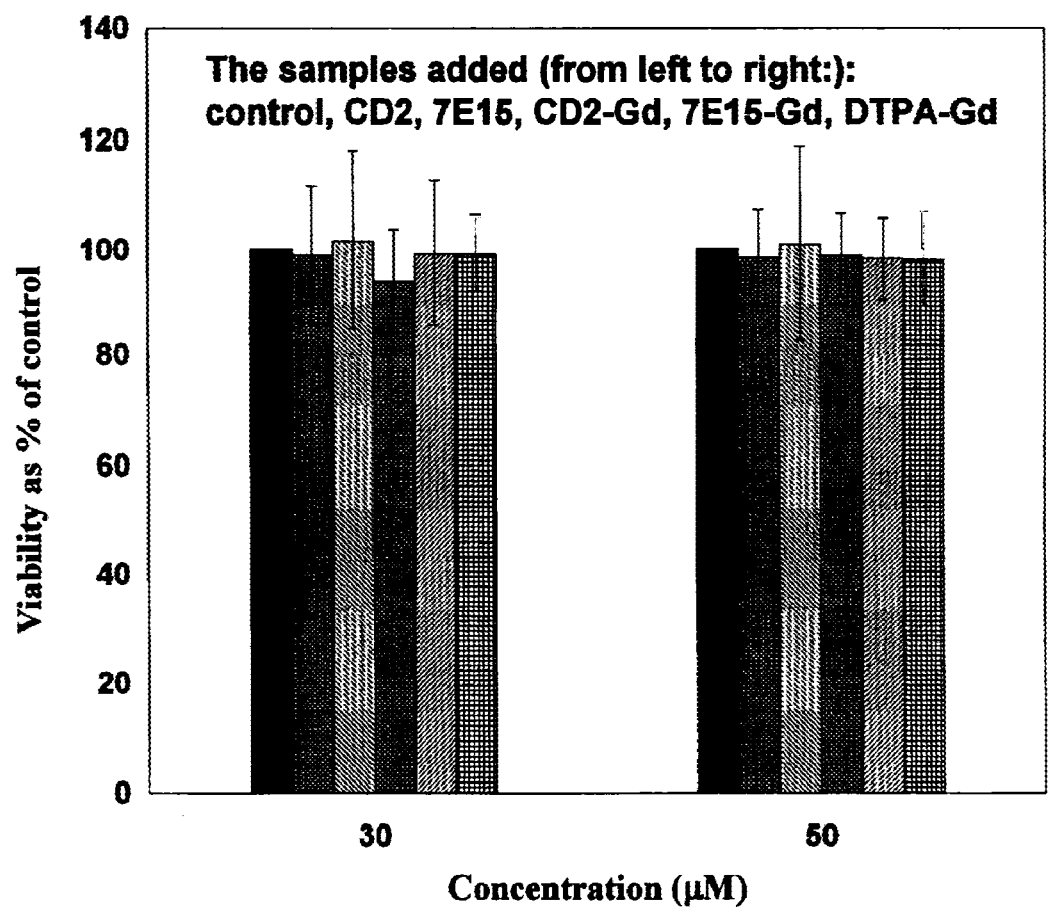
FIG. 6 shows the viability of various contrast agents according to this invention in human serum.

Briefly, testing cells ($1\times10^4$ cells/well in 100 µl medium) were incubated with designed proteins with/without $Gd^{3+}$ (up to 50 µM) for 48 hours. The cell viability was analyzed by MTT assay. No toxicity was observed in any of the tested cells treated with an exemplary contrast agent (e.g. CA1.CD2) with concentrations up to 50 µM. For example, as shown in FIG. 6, no toxicity was observed in all tested cells treated with designed proteins with concentrations up to 50 µM. In addition, the effects of contrast agent on liver enzymes (ALT, ALP, AST, LDH), urea nitrogen, bilirubin, and total protein from CD1 mice 48 hours post-contrast injection was found to be negligible compared to a control subject. Furthermore, no acute toxicity was observed for mice after contrast agent injection, suggesting that the contrast agent of this invention are likely to maintain its metal complex stability and strong affinity for $Gd^{3+}$ in vivo.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the

What is claimed is:

1. A method of magnetic resonance imaging using a modified functional probe comprising: administering a modified fluorescent protein having a fluorescent protein and at least one metal chelating binding site, wherein the metal chelating site is incorporated into the internal structure of the fluorescent protein, wherein the modified fluorescent protein is a single amino acid sequence and wherein the probe acts as a contrast agent in generating one or more images of the subject.

2. The method as claimed in claim 1, wherein the relaxivity of the contrast agent is greater than that of the unmodified fluorescent protein.

3. The method as claimed in claim 1, wherein the metal binding site preferentially binds an paramagnetic metal ion selected from the group consisting of Gd(III), Mn(II), Fe(II), Fe(III), Co(II), Co(III), Ni(III), Mo(V), and V(IV).

4. The method as claimed in claim 1, wherein the metal binding site preferentially binds an ion of a metal selected from the group consisting of Lanthanide Series metals.

5. The method as claimed in claim 1, wherein the modified fluorescent protein is a protein that naturally binds metal ion.

6. The method as claimed in claim 1, wherein the modified fluorescent protein is fluorescent protein having a chromophore.

* * * * *